United States Patent
Johnson et al.

(10) Patent No.: US 12,295,716 B2
(45) Date of Patent: May 13, 2025

(54) METHOD FOR RECORDING PROBE MOVEMENT

(71) Applicant: GLOBUS MEDICAL, INC., Audubon, PA (US)

(72) Inventors: Norbert Johnson, North Andover, MA (US); Neil Crawford, Chandler, AZ (US); Weston Healy, Cambridge, MA (US)

(73) Assignee: Globus Medical, Inc., Audubon, PA (US)

( * ) Notice: Subject to any disclaimer, the term of this patent is extended or adjusted under 35 U.S.C. 154(b) by 0 days.

(21) Appl. No.: 18/610,455

(22) Filed: Mar. 20, 2024

(65) Prior Publication Data
US 2024/0215855 A1    Jul. 4, 2024

Related U.S. Application Data

(63) Continuation of application No. 18/057,497, filed on Nov. 21, 2022, now Pat. No. 11,963,755, which is a
(Continued)

(51) Int. Cl.
*A61B 5/06*    (2006.01)
*A61B 17/00*    (2006.01)
(Continued)

(52) U.S. Cl.
CPC .............. *A61B 5/064* (2013.01); *A61B 5/066* (2013.01); *A61B 17/1671* (2013.01);
(Continued)

(58) Field of Classification Search
CPC ......... A61B 5/064; A61B 5/066; A61B 34/20; A61B 34/30; A61B 34/32; A61B 2034/2051; A61B 2034/2055; A61B 2034/2057; A61B 2034/2059; A61B 2034/301; A61B 90/11; A61B 90/96; A61B 90/98; A61B 2090/034; A61B 2090/0811;
(Continued)

(56) References Cited

U.S. PATENT DOCUMENTS

2016/0151120 A1\* 6/2016 Kostrzewski .......... A61B 90/50
                                                                606/130
2017/0209286 A1\* 7/2017 Palmatier ................. A61B 6/12

\* cited by examiner

*Primary Examiner* — Chao Sheng

(57) ABSTRACT

A method and system for determining an extent of matter removed from a targeted anatomical structure are disclosed. The method includes acquiring an initial representation of a targeted anatomical structure and then removing matter from the targeted anatomical structure. An instrument is then navigated within the targeted anatomical structure. The instrument includes a tracking array, and a relative position of the instrument within the targeted anatomical structure is determined by the tracking array. The method includes recording the relative position of the instrument within the targeted anatomical structure to determine a final representation of the targeted anatomical structure. Finally, the method includes determining an extent of matter removed from the targeted anatomical structure by comparing the initial representation of the targeted anatomical structure with the final representation of the targeted anatomical structure. Indicators are provided to convey the extent of matter remaining within the targeted anatomical structure.

20 Claims, 27 Drawing Sheets

Related U.S. Application Data continuation of application No. 15/609,680, filed on May 31, 2017, now Pat. No. 11,589,771, which is a continuation-in-part of application No. 15/157,444, filed on May 18, 2016, now Pat. No. 11,896,446, which is a continuation-in-part of application No. 15/095,883, filed on Apr. 11, 2016, now Pat. No. 10,893,912, which is a continuation-in-part of application No. 14/062,707, filed on Oct. 24, 2013, now Pat. No. 10,357,184, which is a continuation-in-part of application No. 13/924,505, filed on Jun. 21, 2013, now Pat. No. 9,782,229.

(60) Provisional application No. 61/800,527, filed on Mar. 15, 2013, provisional application No. 61/662,702, filed on Jun. 21, 2012.

(51) Int. Cl.

| | | |
|---|---|---|
| *A61B 17/16* | (2006.01) | |
| *A61B 34/20* | (2016.01) | |
| *A61B 34/30* | (2016.01) | |
| *A61B 34/32* | (2016.01) | |
| *A61B 90/00* | (2016.01) | |
| *A61B 90/96* | (2016.01) | |
| *A61B 90/98* | (2016.01) | |
| *A61F 2/46* | (2006.01) | |
| *A61B 17/17* | (2006.01) | |
| *A61B 90/11* | (2016.01) | |
| *A61F 2/30* | (2006.01) | |
| *A61F 2/44* | (2006.01) | |

(52) U.S. Cl.
CPC .............. *A61B 34/20* (2016.02); *A61B 34/30* (2016.02); *A61B 34/32* (2016.02); *A61B 90/96* (2016.02); *A61B 90/98* (2016.02); *A61F 2/4611* (2013.01); *A61B 2017/00876* (2013.01); *A61B 17/1757* (2013.01); *A61B 2034/2051* (2016.02); *A61B 2034/2055* (2016.02); *A61B 2034/2057* (2016.02); *A61B 2034/2059* (2016.02); *A61B 2034/301* (2016.02); *A61B 2090/034* (2016.02); *A61B 2090/0811* (2016.02); *A61B 90/11* (2016.02); *A61B 2090/376* (2016.02); *A61B 2090/3764* (2016.02); *A61B 2090/3937* (2016.02); *A61B 2090/3945* (2016.02); *A61B 2090/3983* (2016.02); *A61F 2002/30538* (2013.01); *A61F 2/4455* (2013.01); *A61F 2/4603* (2013.01); *A61F 2002/4627* (2013.01); *A61F 2002/4632* (2013.01)

(58) Field of Classification Search
CPC ...... A61B 2090/376; A61B 2090/3764; A61B 2090/3937; A61B 2090/3945; A61B 2090/3983; A61B 17/1671; A61B 17/1757; A61B 2017/00876; A61B 2002/30538; A61B 2002/4627; A61B 2002/4632
See application file for complete search history.

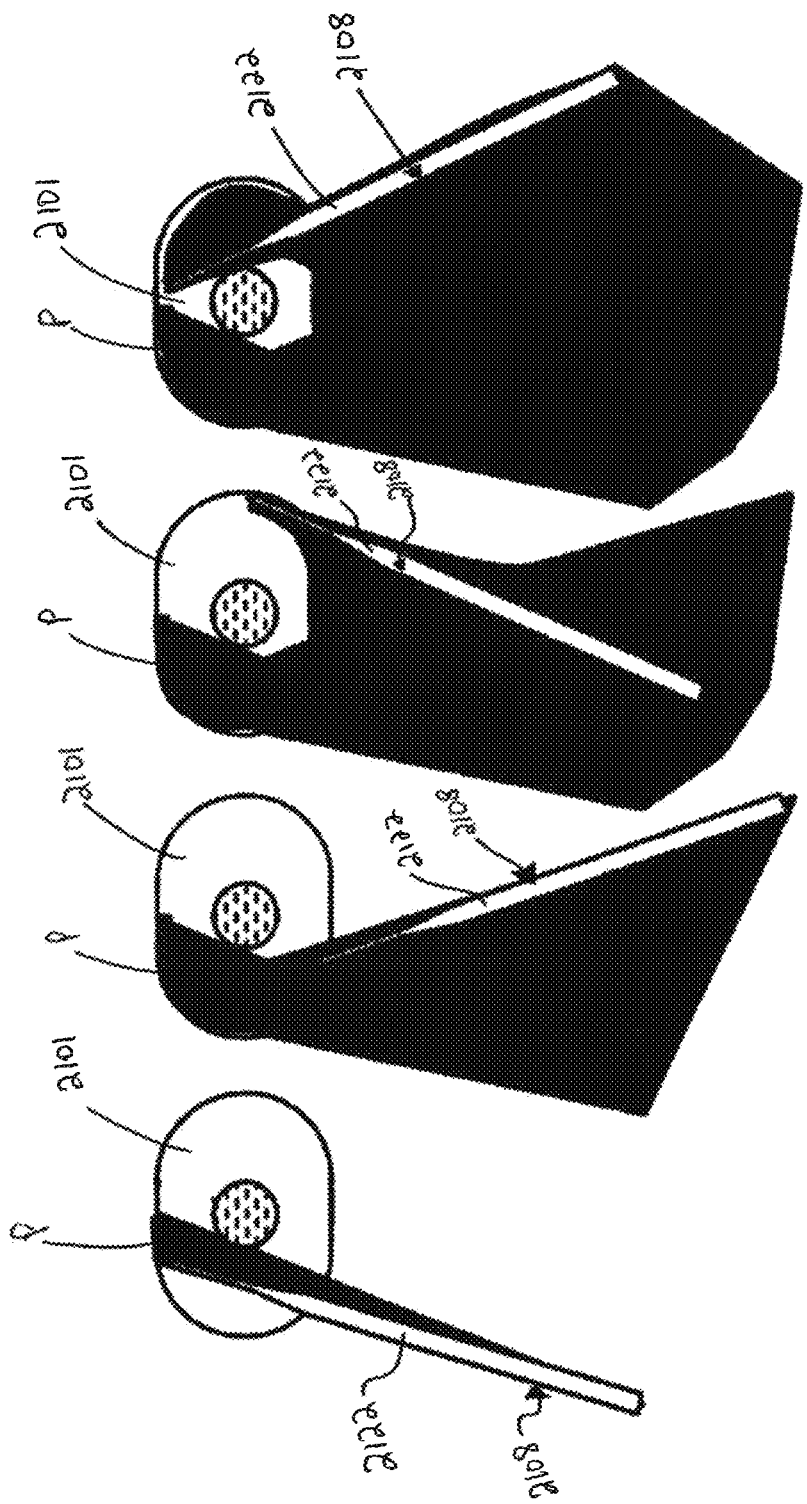

METHOD FOR RECORDING PROBE MOVEMENT

CROSS REFERENCE TO RELATED APPLICATIONS

This application is a continuation of U.S. patent application Ser. No. 18/057,497 filed on Nov. 21, 2022, which is a continuation of U.S. patent application Ser. No. 15/609,680 filed on May 31, 2017, which is a continuation-in-part of U.S. patent application Ser. No. 15/157,444, filed May 18, 2016, which is a continuation-in-part of U.S. patent application Ser. No. 15/095,883, filed Apr. 11, 2016, which is a continuation-in-part of U.S. patent application Ser. No. 14/062,707, filed on Oct. 24, 2013, which is a continuation-in-part application of U.S. patent application Ser. No. 13/924,505, filed on Jun. 21, 2013, which claims priority to provisional application No. 61/662,702 filed on Jun. 21, 2012 and claims priority to provisional application No. 61/800,527 filed on Mar. 15, 2013, all of which are incorporated by reference herein in their entireties for all purposes.

FIELD

The present disclosure relates to a position recognition system, and in particular, a probing system for determining an extent of matter in a targeted anatomical structure.

BACKGROUND

Certain surgical procedures require a surgeon to remove matter, i.e. bone or tissue, from a patient. During spinal implant surgeries, a surgeon typically must first remove a disk, including primarily ligament and cartilage, from the patient's spine to provide a clear installation site for attaching an implant or replacement disk to the spine. Surgeons typically perform this removal process without the aid of any real-time indicator to demonstrate how much matter remains in the patient's targeted anatomical structure. The surgeon must develop a tactile feel for how an instrument navigates through the targeted anatomical structure, and rely on this tactile feel to make a determination regarding how much matter remains in the targeted anatomical structure. The surgeon must also develop a mental image or map of the targeted anatomical structure based on how the instrument feels while being navigated through the targeted anatomical structure. Due to potential "blind spots," the surgeon can navigate an instrument through the targeted anatomical structure and mistakenly conclude that the proposed installation site is clear of extraneous bone or tissue. This false conclusion can result in the surgeon proceeding with attempting to install an implant despite the installation site not being sufficiently cleared. Alternatively, the surgeon may begin the installation procedure, only to realize that the installation site is not cleared, causing the installation procedure to be delayed until additional matter is removed from the installation site.

It would be desirable to provide a more dependable way for a surgeon to ensure that a targeted anatomical structure is sufficiently clear of matter following a targeted removal procedure.

SUMMARY

To meet this and other needs, devices, systems, and methods for determining an extent of matter remaining within a targeted anatomical structure are provided.

In one embodiment, a method for determining an extent of matter removed from a targeted anatomical structure is provided. The method includes acquiring an initial representation of a targeted anatomical structure and then removing matter from the targeted anatomical structure. An instrument is then navigated within the targeted anatomical structure. The instrument includes a tracking array, and a relative position of the instrument within the targeted anatomical structure is determined by the tracking array. The method includes recording the relative position of the instrument within the targeted anatomical structure to determine a final representation of the targeted anatomical structure. Finally, the method includes determining an extent of matter removed from the targeted anatomical structure by comparing the initial representation of the targeted anatomical structure with the final representation of the targeted anatomical structure.

In one embodiment, a tracking system for determining an extent of matter remaining in a targeted anatomical structure is provided. The system includes an instrument including a tracking array, and the instrument is configured to be received within a targeted anatomical structure. The system includes at least one camera that detects a relative position of the instrument within the targeted anatomical structure via the tracking array. A computer system includes a display, and the computer system records the relative position of the instrument within the targeted anatomical structure. The display illustrates a path of the instrument within the targeted anatomical structure relative to an initial representation of the targeted anatomical structure. A surgeon can rely on this mapped path of the instrument to conclude how much matter has been removed from the targeted anatomical structure.

DESCRIPTION OF THE DRAWINGS

FIGS. 21A-21D illustrate a system of determining an extent of matter remaining in a targeted anatomical structure according to one embodiment in which a shaft of the instrument is tracked. FIG. 21A shows the beginning of the tracing of a path around the perimeter of the disc, progressing through FIG. 21B and FIG. 21C and ending at FIG. 21D with the perimeter fully traced. The space that was occupied by the shaft during tracing is illustrated in black.

DETAILED DESCRIPTION

Figure 1:
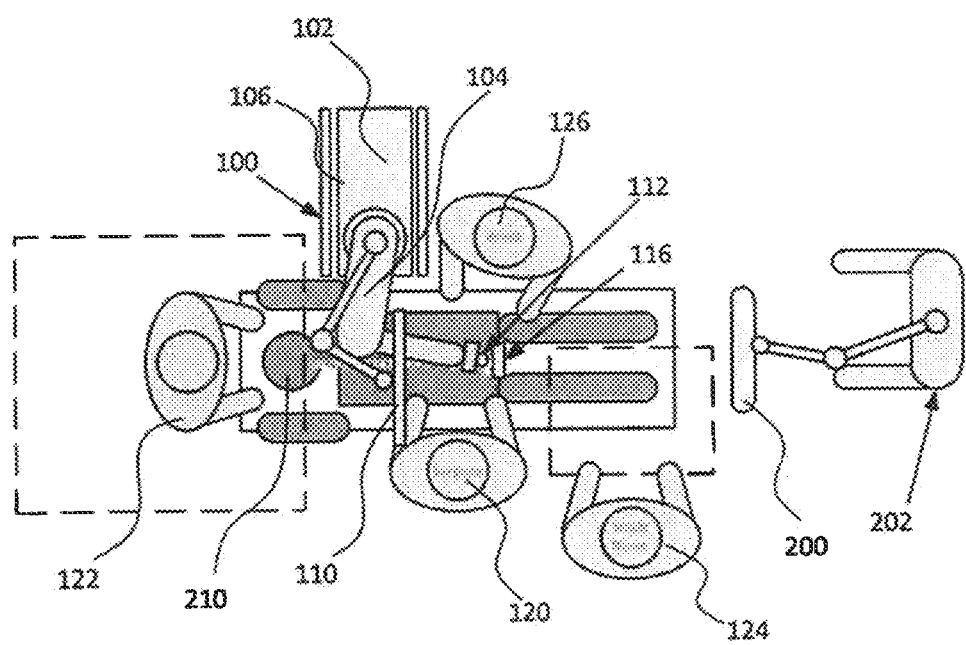
FIG. 1 is an overhead view of a potential arrangement for locations of the robotic system, patient, surgeon, and other medical personnel during a surgical procedure.

It is to be understood that the present disclosure is not limited in its application to the details of construction and the arrangement of components set forth in the description herein or illustrated in the drawings. The teachings of the present disclosure may be used and practiced in other embodiments and practiced or carried out in various ways. Also, it is to be understood that the phraseology and terminology used herein is for the purpose of description and should not be regarded as limiting. The use of "including," "comprising," or "having" and variations thereof herein is meant to encompass the items listed thereafter and equivalents thereof as well as additional items. Unless specified or limited otherwise, the terms "mounted," "connected," "supported," and "coupled" and variations thereof are used broadly and encompass both direct and indirect mountings, connections, supports, and couplings. Further, "connected" and "coupled" are not restricted to physical or mechanical connections or couplings.

The following discussion is presented to enable a person skilled in the art to make and use embodiments of the present disclosure. Various modifications to the illustrated embodiments will be readily apparent to those skilled in the art, and the principles herein can be applied to other embodiments and applications without departing from embodiments of the present disclosure. Thus, the embodiments are not intended to be limited to embodiments shown, but are to be accorded the widest scope consistent with the principles and features disclosed herein. The following detailed description is to be read with reference to the figures, in which like elements in different figures have like reference numerals. The figures, which are not necessarily to scale, depict selected embodiments and are not intended to limit the scope of the embodiments. Skilled artisans will recognize the examples provided herein have many useful alternatives and fall within the scope of the embodiments.

Figure 2:
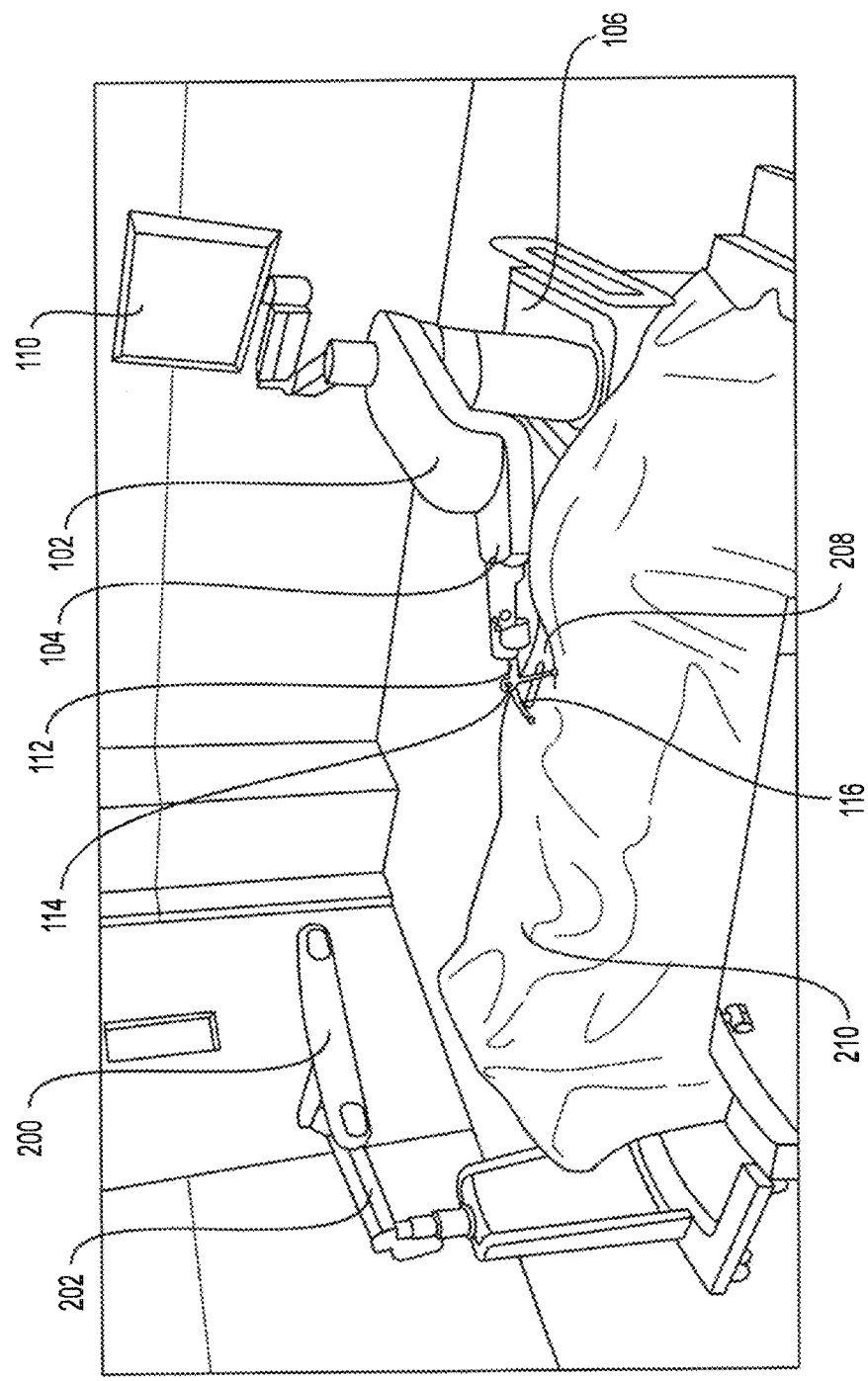
FIG. 2 illustrates the robotic system including positioning of the surgical robot and the camera relative to the patient according to one embodiment.

Turning now to the drawing, FIGS. 1 and 2 illustrate a surgical robot system 100 in accordance with an exemplary embodiment. Surgical robot system 100 may include, for example, a surgical robot 102, one or more robot arms 104, a base 106, a display 110, an end-effector 112, for example, including a guide tube 114, and one or more tracking markers 118. The surgical robot system 100 may include a patient tracking device 116 also including one or more tracking markers 118, which is adapted to be secured directly to the patient 210 (e.g., to the bone of the patient 210). The surgical robot system 100 may also utilize a camera 200, for example, positioned on a camera stand 202. The camera stand 202 can have any suitable configuration to move, orient, and support the camera 200 in a desired position. The camera 200 may include any suitable camera or cameras, such as one or more infrared cameras (e.g., bifocal or stereophotogrammetric cameras), able to identify, for example, active and passive tracking markers 118 in a given measurement volume viewable from the perspective of the camera 200. The camera 200 may scan the given measurement volume and detect the light that comes from the markers 118 in order to identify and determine the position of the markers 118 in three-dimensions. For example, active markers 118 may include infrared-emitting markers that are activated by an electrical signal (e.g., infrared light emitting diodes (LEDs)), and passive markers 118 may include retro-reflective markers that reflect infrared light (e.g., they reflect incoming IR radiation into the direction of the incoming light), for example, emitted by illuminators on the camera 200 or other suitable device.

FIGS. 1 and 2 illustrate a potential configuration for the placement of the surgical robot system 100 in an operating room environment. For example, the robot 102 may be positioned near or next to patient 210. Although depicted near the head of the patient 210, it will be appreciated that the robot 102 can be positioned at any suitable location near the patient 210 depending on the area of the patient 210 undergoing the operation. The camera 200 may be separated from the robot system 100 and positioned at the foot of patient 210. This location allows the camera 200 to have a direct visual line of sight to the surgical field 208. Again, it is contemplated that the camera 200 may be located at any suitable position having line of sight to the surgical field 208. In the configuration shown, the surgeon 120 may be positioned across from the robot 102, but is still able to manipulate the end-effector 112 and the display 110. A surgical assistant 126 may be positioned across from the surgeon 120 again with access to both the end-effector 112 and the display 110. If desired, the locations of the surgeon 120 and the assistant 126 may be reversed. The traditional areas for the anesthesiologist 122 and the nurse or scrub tech 124 remain unimpeded by the locations of the robot 102 and camera 200.

With respect to the other components of the robot 102, the display 110 can be attached to the surgical robot 102 and in other exemplary embodiments, display 110 can be detached from surgical robot 102, either within a surgical room with the surgical robot 102, or in a remote location. End-effector 112 may be coupled to the robot arm 104 and controlled by at least one motor. In exemplary embodiments, end-effector 112 can comprise a guide tube 114, which is able to receive and orient a surgical instrument 608 (described further herein) used to perform surgery on the patient 210. As used herein, the term "end-effector" is used interchangeably with the terms "end-effectuator" and "effectuator element." Although generally shown with a guide tube 114, it will be appreciated that the end-effector 112 may be replaced with any suitable instrumentation suitable for use in surgery. In some embodiments, end-effector 112 can comprise any known structure for effecting the movement of the surgical instrument 608 in a desired manner.

The surgical robot 102 is able to control the translation and orientation of the end-effector 112. The robot 102 is able to move end-effector 112 along x-, y-, and z-axes, for example. The end-effector 112 can be configured for selective rotation about one or more of the x-, y-, and z-axis, and a Z Frame axis (such that one or more of the Euler Angles (e.g., roll, pitch, and/or yaw) associated with end-effector 112 can be selectively controlled). In some exemplary embodiments, selective control of the translation and orientation of end-effector 112 can permit performance of medical procedures with significantly improved accuracy compared to conventional robots that utilize, for example, a six degree of freedom robot arm comprising only rotational axes. For example, the surgical robot system 100 may be used to operate on patient 210, and robot arm 104 can be positioned above the body of patient 210, with end-effector 112 selectively angled relative to the z-axis toward the body of patient 210.

In some exemplary embodiments, the position of the surgical instrument 608 can be dynamically updated so that surgical robot 102 can be aware of the location of the surgical instrument 608 at all times during the procedure. Consequently, in some exemplary embodiments, surgical robot 102 can move the surgical instrument 608 to the desired position quickly without any further assistance from a physician (unless the physician so desires). In some further embodiments, surgical robot 102 can be configured to correct the path of the surgical instrument 608 if the surgical instrument 608 strays from the selected, preplanned trajectory. In some exemplary embodiments, surgical robot 102 can be configured to permit stoppage, modification, and/or manual control of the movement of end-effector 112 and/or the surgical instrument 608. Thus, in use, in exemplary embodiments, a physician or other user can operate the system 100, and has the option to stop, modify, or manually control the autonomous movement of end-effector 112 and/or the surgical instrument 608. Further details of surgical robot system 100 including the control and movement of a surgical instrument 608 by surgical robot 102 can be found in co-pending U.S. patent application Ser. No. 13/924,505, which is incorporated herein by reference in its entirety.

The robotic surgical system 100 can comprise one or more tracking markers 118 configured to track the movement of robot arm 104, end-effector 112, patient 210, and/or the surgical instrument 608 in three dimensions. In exemplary embodiments, a plurality of tracking markers 118 can be mounted (or otherwise secured) thereon to an outer surface of the robot 102, such as, for example and without limitation, on base 106 of robot 102, on robot arm 104, or on the end-effector 112. In exemplary embodiments, at least one tracking marker 118 of the plurality of tracking markers 118 can be mounted or otherwise secured to the end-effector 112. One or more tracking markers 118 can further be mounted (or otherwise secured) to the patient 210. In exemplary embodiments, the plurality of tracking markers 118 can be positioned on the patient 210 spaced apart from the surgical field 208 to reduce the likelihood of being obscured by the surgeon, surgical tools, or other parts of the robot 102. Further, one or more tracking markers 118 can be further mounted (or otherwise secured) to the surgical tools 608 (e.g., a screw driver, dilator, implant inserter, or the like). Thus, the tracking markers 118 enable each of the marked objects (e.g., the end-effector 112, the patient 210, and the surgical tools 608) to be tracked by the robot 102. In exemplary embodiments, system 100 can use tracking information collected from each of the marked objects to calculate the orientation and location, for example, of the end-effector 112, the surgical instrument 608 (e.g., positioned in the tube 114 of the end-effector 112), and the relative position of the patient 210.

In exemplary embodiments, one or more of markers 118 may be optical markers. In some embodiments, the positioning of one or more tracking markers 118 on end-effector 112 can maximize the accuracy of the positional measurements by serving to check or verify the position of end-effector 112. Further details of surgical robot system 100 including the control, movement and tracking of surgical robot 102 and of a surgical instrument 608 can be found in co-pending U.S. patent application Ser. No. 13/924,505, which is incorporated herein by reference in its entirety.

Exemplary embodiments include one or more markers 118 coupled to the surgical instrument 608. In exemplary embodiments, these markers 118, for example, coupled to the patient 210 and surgical instruments 608, as well as markers 118 coupled to the end-effector 112 of the robot 102 can comprise conventional infrared light-emitting diodes (LEDs) or an Optotrak® diode capable of being tracked using a commercially available infrared optical tracking system such as Optotrak®. Optotrak® is a registered trademark of Northern Digital Inc., Waterloo, Ontario, Canada. In other embodiments, markers 118 can comprise conventional reflective spheres capable of being tracked using a commercially available optical tracking system such as Polaris Spectra. Polaris Spectra is also a registered trademark of Northern Digital, Inc. In an exemplary embodiment, the markers 118 coupled to the end-effector 112 are active markers which comprise infrared light-emitting diodes which may be turned on and off, and the markers 118 coupled to the patient 210 and the surgical instruments 608 comprise passive reflective spheres.

In exemplary embodiments, light emitted from and/or reflected by markers 118 can be detected by camera 200 and can be used to monitor the location and movement of the marked objects. In alternative embodiments, markers 118 can comprise a radio-frequency and/or electromagnetic reflector or transceiver and the camera 200 can include or be replaced by a radio-frequency and/or electromagnetic transceiver.

Figure 3:
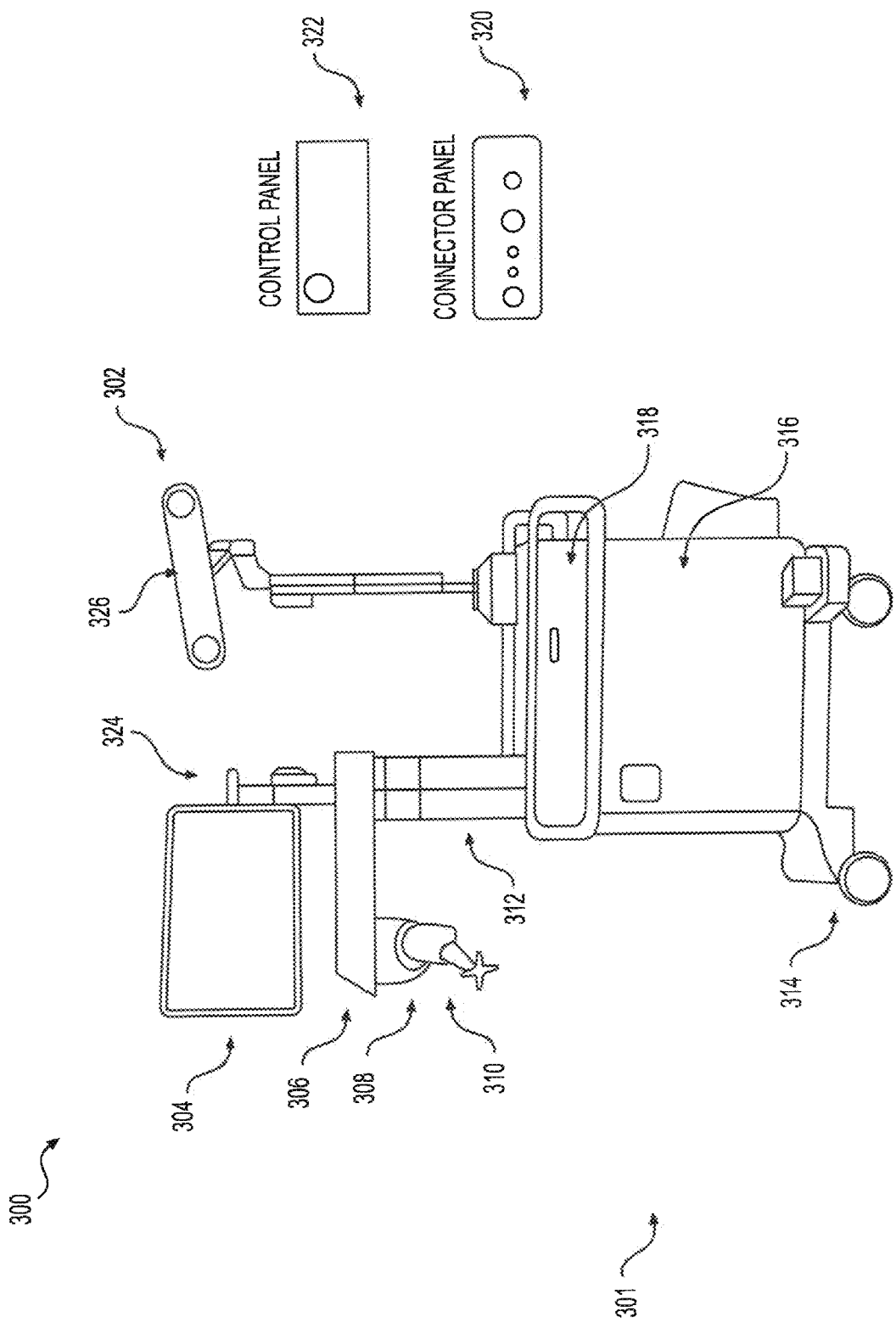
FIG. 3 illustrates a surgical robotic system in accordance with an exemplary embodiment.

Similar to surgical robot system 100, FIG. 3 illustrates a surgical robot system 300 and camera stand 302, in a docked configuration, consistent with an exemplary embodiment of the present disclosure. Surgical robot system 300 may comprise a robot 301 including a display 304, upper arm 306, lower arm 308, end-effector 310, vertical column 312, casters 314, cabinet 316, tablet drawer 318, connector panel 320, control panel 322, and ring of information 324. Camera stand 302 may comprise camera 326. These components are described in greater with respect to FIG. 5. FIG. 3 illustrates the surgical robot system 300 in a docked configuration where the camera stand 302 is nested with the robot 301, for example, when not in use. It will be appreciated by those skilled in the art that the camera 326 and robot 301 may be separated from one another and positioned at any appropriate location during the surgical procedure, for example, as shown in FIGS. 1 and 2.

Figure 4:
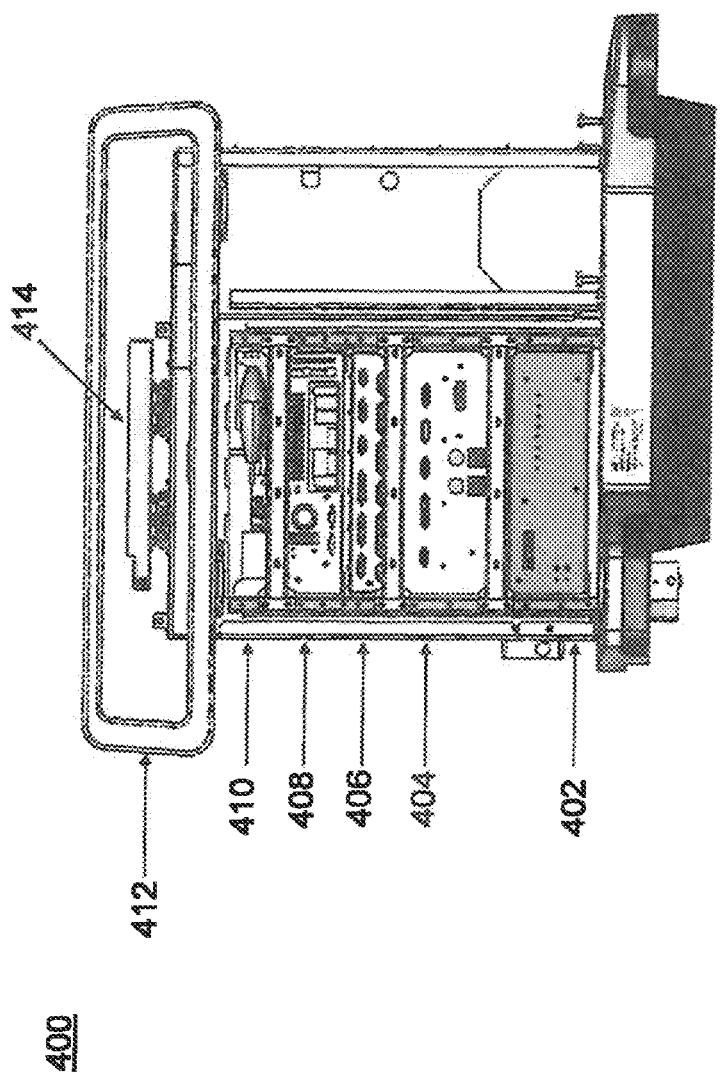
FIG. 4 illustrates a portion of a surgical robot in accordance with an exemplary embodiment.

FIG. 4 illustrates a base 400 consistent with an exemplary embodiment of the present disclosure. Base 400 may be a portion of surgical robot system 300 and comprise cabinet 316. Cabinet 316 may house certain components of surgical robot system 300 including but not limited to a battery 402, a power distribution module 404, a platform interface board module 406, a computer 408, a handle 412, and a tablet drawer 414. The connections and relationship between these components is described in greater detail with respect to FIG. 5.

Figure 5:
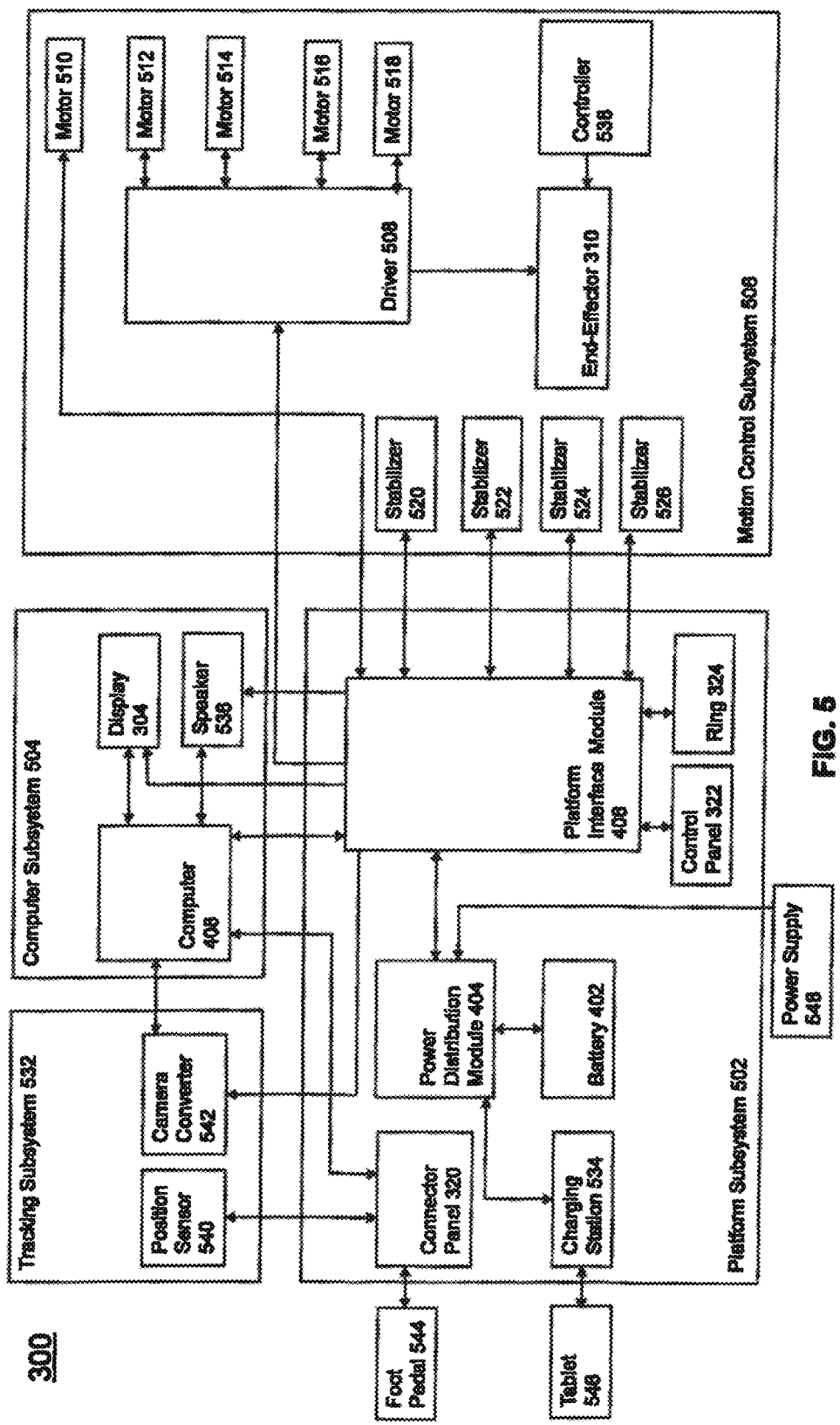
FIG. 5 illustrates a block diagram of a surgical robot in accordance with an exemplary embodiment.

FIG. 5 illustrates a block diagram of certain components of an exemplary embodiment of surgical robot system 300. Surgical robot system 300 may comprise platform subsystem 502, computer subsystem 504, motion control subsystem 506, and tracking subsystem 532. Platform subsystem 502 may further comprise battery 402, power distribution module 404, platform interface board module 406, and tablet charging station 534. Computer subsystem 504 may further comprise computer 408, display 304, and speaker 536. Motion control subsystem 506 may further comprise driver circuit 508, motors 510, 512, 514, 516, 518, stabilizers 520, 522, 524, 526, end-effector 310, and controller 538. Tracking subsystem 532 may further comprise position sensor 540 and camera converter 542. System 300 may also comprise a foot pedal 544 and tablet 546.

Input power is supplied to system 300 via a power source 548 which may be provided to power distribution module 404. Power distribution module 404 receives input power and is configured to generate different power supply voltages that are provided to other modules, components, and subsystems of system 300. Power distribution module 404 may be configured to provide different voltage supplies to platform interface module 406, which may be provided to other components such as computer 408, display 304, speaker 536, driver 508 to, for example, power motors 512, 514, 516, 518 and end-effector 310, motor 510, ring 324, camera converter 542, and other components for system 300 for example, fans for cooling the electrical components within cabinet 316.

Power distribution module 404 may also provide power to other components such as tablet charging station 534 that may be located within tablet drawer 318. Tablet charging station 534 may be in wireless or wired communication with tablet 546 for charging table 546. Tablet 546 may be used by a surgeon consistent with the present disclosure and described herein.

Power distribution module 404 may also be connected to battery 402, which serves as temporary power source in the event that power distribution module 404 does not receive power from input power 548. At other times, power distribution module 404 may serve to charge battery 402 if necessary.

Other components of platform subsystem 502 may also include connector panel 320, control panel 322, and ring 324. Connector panel 320 may serve to connect different devices and components to system 300 and/or associated components and modules. Connector panel 320 may contain one or more ports that receive lines or connections from different components. For example, connector panel 320 may have a ground terminal port that may ground system 300 to other equipment, a port to connect foot pedal 544 to system 300, a port to connect to tracking subsystem 532, which may comprise position sensor 540, camera converter 542, and cameras 326 associated with camera stand 302. Connector panel 320 may also include other ports to allow USB, Ethernet, HDMI communications to other components, such as computer 408.

Control panel 322 may provide various buttons or indicators that control operation of system 300 and/or provide information regarding system 300. For example, control panel 322 may include buttons to power on or off system 300, lift or lower vertical column 312, and lift or lower stabilizers 520-526 that may be designed to engage casters 314 to lock system 300 from physically moving. Other buttons may stop system 300 in the event of an emergency, which may remove all motor power and apply mechanical brakes to stop all motion from occurring. Control panel 322 may also have indicators notifying the user of certain system conditions such as a line power indicator or status of charge for battery 402.

Ring 324 may be a visual indicator to notify the user of system 300 of different modes that system 300 is operating under and certain warnings to the user.

Computer subsystem 504 includes computer 408, display 304, and speaker 536. Computer 504 includes an operating system and software to operate system 300. Computer 504 may receive and process information from other components (for example, tracking subsystem 532, platform subsystem 502, and/or motion control subsystem 506) in order to display information to the user. Further, computer subsystem 504 may also include speaker 536 to provide audio to the user.

Tracking subsystem 532 may include position sensor 504 and converter 542. Tracking subsystem 532 may correspond to camera stand 302 including camera 326 as described with respect to FIG. 3. Position sensor 504 may be camera 326. Tracking subsystem may track the location of certain markers that are located on the different components of system 300 and/or instruments used by a user during a surgical procedure. This tracking may be conducted in a manner consistent with the present disclosure including the use of infrared technology that tracks the location of active or passive elements, such as LEDs or reflective markers, respectively. The location, orientation, and position of structures having these types of markers may be provided to computer 408 which may be shown to a user on display 304.

For example, a surgical instrument 608 having these types of markers and tracked in this manner (which may be referred to as a navigational space) may be shown to a user in relation to a three dimensional image of a patient's anatomical structure.

Motion control subsystem 506 may be configured to physically move vertical column 312, upper arm 306, lower arm 308, or rotate end-effector 310. The physical movement may be conducted through the use of one or more motors 510-518. For example, motor 510 may be configured to vertically lift or lower vertical column 312. Motor 512 may be configured to laterally move upper arm 308 around a point of engagement with vertical column 312 as shown in FIG. 3.

Motor 514 may be configured to laterally move lower arm 308 around a point of engagement with upper arm 308 as shown in FIG. 3. Motors 516 and 518 may be configured to move end-effector 310 in a manner such that one may control the roll and one may control the tilt, thereby providing multiple angles that end-effector 310 may be moved. These movements may be achieved by controller 538 which may control these movements through load cells disposed on end-effector 310 and activated by a user engaging these load cells to move system 300 in a desired manner.

Moreover, system 300 may provide for automatic movement of vertical column 312, upper arm 306, and lower arm 308 through a user indicating on display 304 (which may be a touchscreen input device) the location of a surgical instrument or component on three dimensional image of the patient's anatomy on display 304. The user may initiate this automatic movement by stepping on foot pedal 544 or some other input means.

Figure 6:
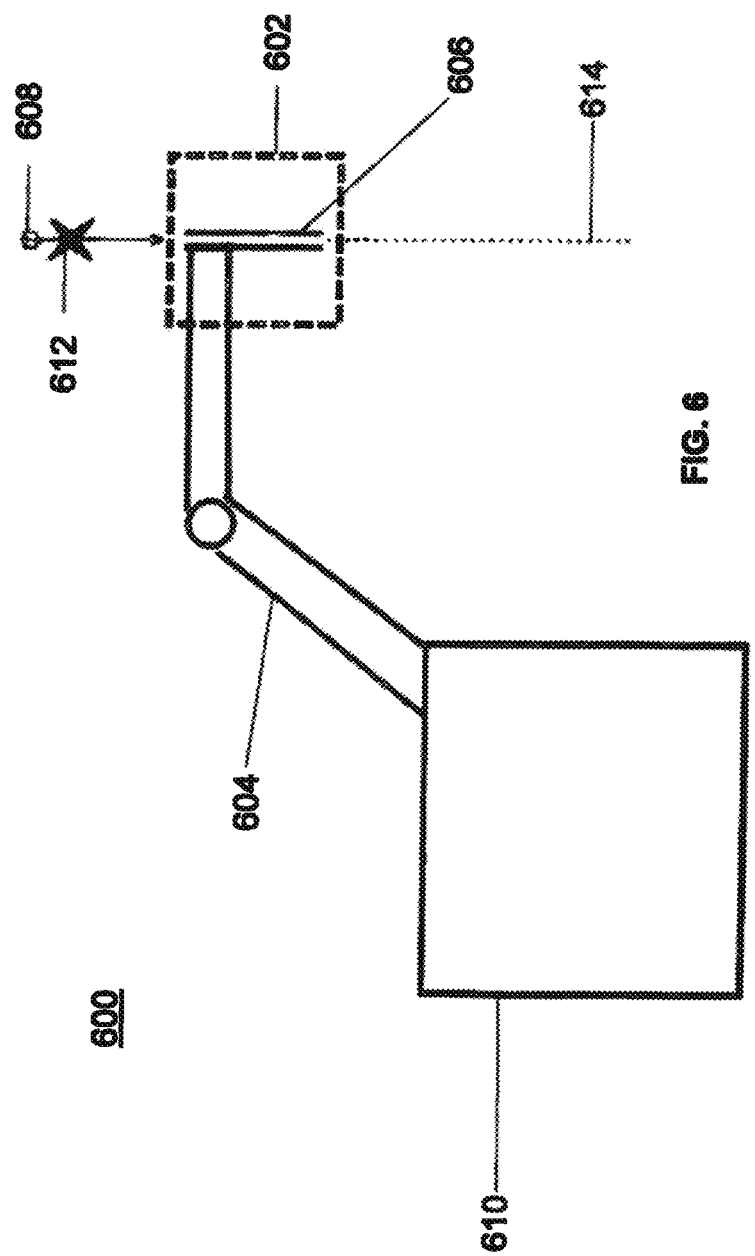
FIG. 6 illustrates a surgical robot in accordance with an exemplary embodiment.

FIG. 6 illustrates a surgical robot system 600 consistent with an exemplary embodiment. Surgical robot system 600 may comprise end-effector 602, robot arm 604, guide tube 606, instrument 608, and robot base 610. Instrument tool 608 may be attached to a tracking array 612 including one or more tracking markers (such as markers 118) and have an associated trajectory 614. Trajectory 614 may represent a path of movement that instrument tool 608 is configured to travel once it is positioned through or secured in guide tube 606, for example, a path of insertion of instrument tool 608 into a patient. In an exemplary operation, robot base 610 may be configured to be in electronic communication with robot arm 604 and end-effector 602 so that surgical robot system 600 may assist a user (for example, a surgeon) in operating on the patient 210. Surgical robot system 600 may be consistent with previously described surgical robot system 100 and 300.

Figure 8:
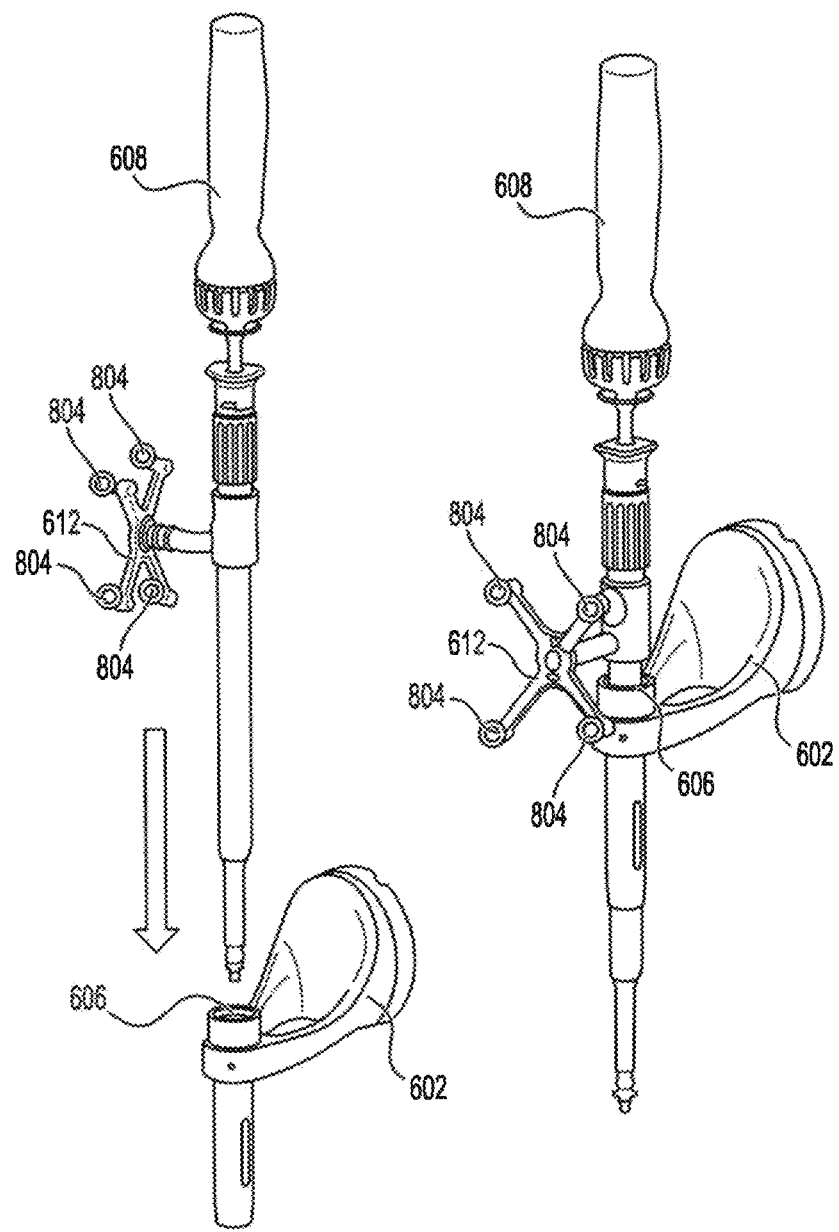
FIG. 8 illustrates a surgical instrument and the end-effector, before and after, inserting the surgical instrument into the guide tube of the end-effector according to one embodiment.

A tracking array 612 may be mounted on instrument 608 to monitor the location and orientation of instrument tool 608. The tracking array 612 may be attached to an instrument 608 and may comprise tracking markers 804. As best seen in FIG. 8, tracking markers 804 may be, for example, light emitting diodes and/or other types of reflective markers (e.g., markers 118 as described elsewhere herein). The tracking devices may be one or more line of sight devices associated with the surgical robot system. As an example, the tracking devices may be one or more cameras 200, 326 associated with the surgical robot system 100, 300 and may also track tracking array 612 for a defined domain or relative orientations of the instrument 608 in relation to the robot arm 604, the robot base 610, end-effector 602, and/or the patient 210. The tracking devices may be consistent with those structures described in connection with camera stand 302 and tracking subsystem 532.

Figure 7:
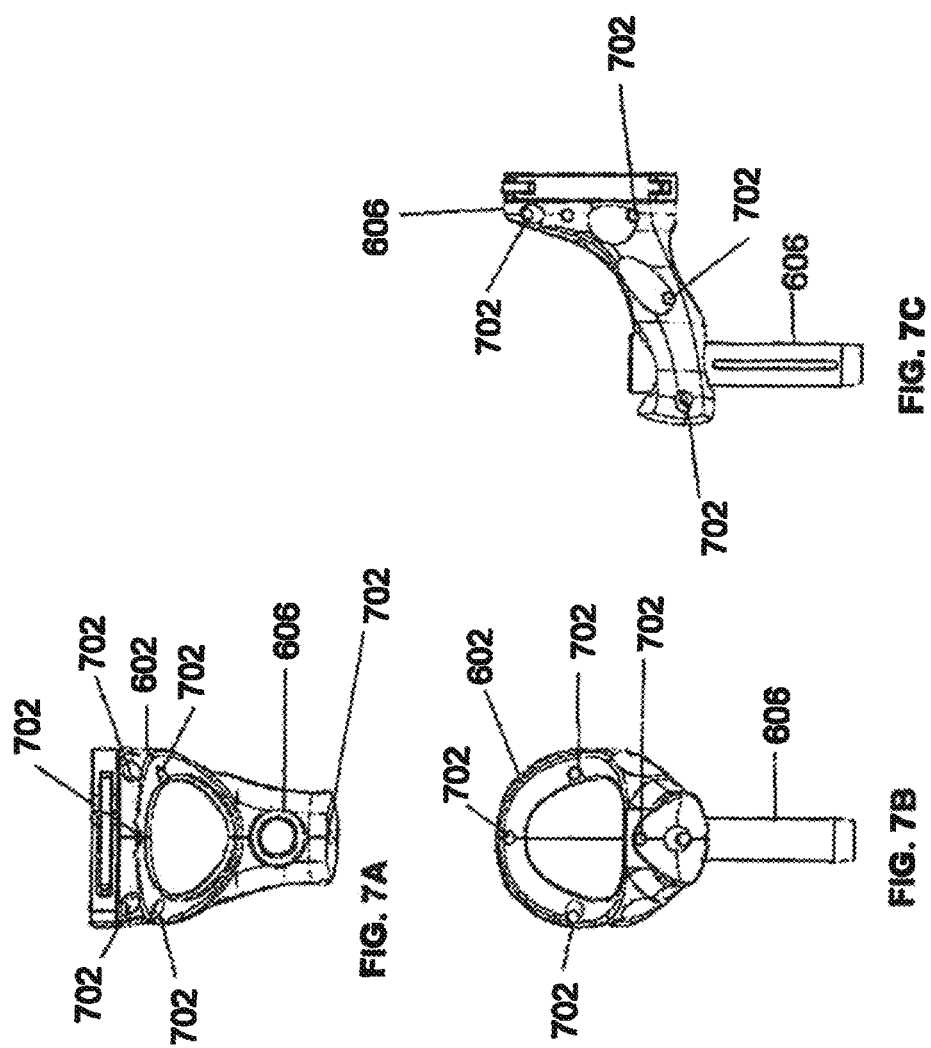
FIGS. 7A-7C illustrate an end-effector in accordance with an exemplary embodiment.

FIGS. 7A, 7B, and 7C illustrate a top view, front view, and side view, respectively, of end-effector 602 consistent with an exemplary embodiment. End-effector 602 may comprise one or more tracking markers 702. Tracking markers 702 may be light emitting diodes or other types of active and passive markers, such as tracking markers 118 that have been previously described. In an exemplary embodiment, the tracking markers 702 are active infrared-emitting markers that are activated by an electrical signal (e.g., infrared light emitting diodes (LEDs)). Thus, tracking markers 702 may be activated such that the infrared markers 702 are visible to the camera 200, 326 or may be deactivated such that the infrared markers 702 are not visible to the camera 200, 326. Thus, when the markers 702 are active, the end-effector 602 may be controlled by the system 100, 300, 600, and when the markers 702 are deactivated, the end-effector 602 may be locked in position and unable to be moved by the system 100, 300, 600.

Markers 702 may be disposed on or within end-effector 602 in a manner such that the markers 702 are visible by one or more cameras 200, 326 or other tracking devices associated with the surgical robot system 100, 300, 600. The camera 200, 326 or other tracking devices may track end-effector 602 as it moves to different positions and viewing angles by following the movement of tracking markers 702. The location of markers 702 and/or end-effector 602 may be shown on a display 110, 304 associated with the surgical robot system 100, 300, 600, for example, display 110 as shown in FIG. 2 and/or display 304 shown in FIG. 3. This display 110, 304 may allow a user to ensure that end-effector 602 is in a desirable position in relation to robot arm 604, robot base 610, the patient 210, and/or the user.

For example, as shown in FIG. 7A, markers 702 may be placed around the surface of end-effector 602 so that a tracking device placed away from the surgical field 208 and facing toward the robot 102, 301 and the camera 200, 326 is able to view at least 3 of the markers 702 through a range of common orientations of the end-effector 602 relative to the tracking device 100, 300, 600. For example, distribution of markers 702 in this way allows end-effector 602 to be monitored by the tracking devices when end-effector 602 is translated and rotated in the surgical field 208.

In addition, in exemplary embodiments, end-effector 602 may be equipped with infrared (IR) receivers that can detect when an external camera 200, 326 is getting ready to read markers 702. Upon this detection, end-effector 602 may then illuminate markers 702. The detection by the IR receivers that the external camera 200, 326 is ready to read markers 702 may signal the need to synchronize a duty cycle of markers 702, which may be light emitting diodes, to an external camera 200, 326. This may also allow for lower power consumption by the robotic system as a whole, whereby markers 702 would only be illuminated at the appropriate time instead of being illuminated continuously. Further, in exemplary embodiments, markers 702 may be powered off to prevent interference with other navigation tools, such as different types of surgical instruments 608.

FIG. 8 depicts one type of surgical instrument 608 including a tracking array 612 and tracking markers 804. Tracking markers 804 may be of any type described herein including but not limited to light emitting diodes or reflective spheres. Markers 804 are monitored by tracking devices associated with the surgical robot system 100, 300, 600 and may be one or more of the line of sight cameras 200, 326. The cameras 200, 326 may track the location of instrument 608 based on the position and orientation of tracking array 612 and markers 804. A user, such as a surgeon 120, may orient instrument 608 in a manner so that tracking array 612 and markers 804 are sufficiently recognized by the tracking device or camera 200, 326 to display instrument 608 and markers 804 on, for example, display 110 of the exemplary surgical robot system.

The manner in which a surgeon 120 may place instrument 608 into guide tube 606 of the end-effector 602 and adjust the instrument 608 is evident in FIG. 8. The hollow tube or guide tube 114, 606 of the end-effector 112, 310, 602 is sized and configured to receive at least a portion of the surgical instrument 608. The guide tube 114, 606 is configured to be oriented by the robot arm 104 such that insertion and trajectory for the surgical instrument 608 is able to reach a desired anatomical target within or upon the body of the patient 210. The surgical instrument 608 may include at least a portion of a generally cylindrical instrument. Although a screw driver is exemplified as the surgical tool 608, it will be appreciated that any suitable surgical tool 608 may be positioned by the end-effector 602. By way of example, the surgical instrument 608 may include one or more of a guide wire, cannula, a retractor, a drill, a reamer, a screw driver, an insertion tool, a removal tool, or the like. Although the hollow tube 114, 606 is generally shown as having a cylindrical configuration, it will be appreciated by those of skill in the art that the guide tube 114, 606 may have any suitable shape, size and configuration desired to accommodate the surgical instrument 608 and access the surgical site.

Figure 9:
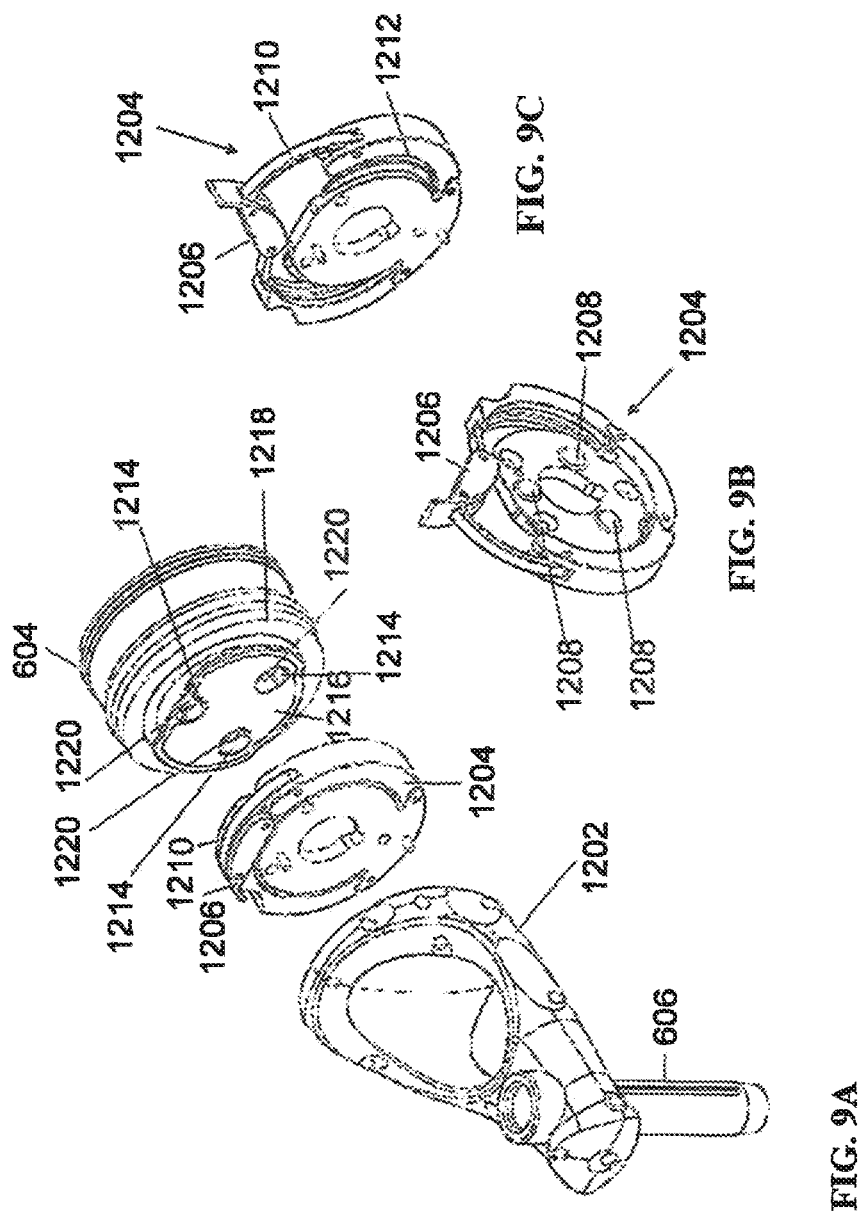
FIGS. 9A-9C illustrate portions of an end-effector and robot arm in accordance with an exemplary embodiment.

FIGS. 9A-9C illustrate end-effector 602 and a portion of robot arm 604 consistent with an exemplary embodiment. End-effector 602 may further comprise body 1202 and clamp 1204. Clamp 1204 may comprise handle 1206, balls 1208, spring 1210, and lip 1212. Robot arm 604 may further comprise depressions 1214, mounting plate 1216, lip 1218, and magnets 1220.

End-effector 602 may mechanically interface and/or engage with the surgical robot system and robot arm 604 through one or more couplings. For example, end-effector 602 may engage with robot arm 604 through a locating coupling and/or a reinforcing coupling. Through these couplings, end-effector 602 may fasten with robot arm 604 outside a flexible and sterile barrier. In an exemplary embodiment, the locating coupling may be a magnetically kinematic mount and the reinforcing coupling may be a five bar over center clamping linkage.

With respect to the locating coupling, robot arm 604 may comprise mounting plate 1216, which may be non-magnetic material, one or more depressions 1214, lip 1218, and magnets 1220. Magnet 1220 is mounted below each of depressions 1214. Portions of clamp 1204 may comprise magnetic material and be attracted by one or more magnets 1220. Through the magnetic attraction of clamp 1204 and robot arm 604, balls 1208 become seated into respective depressions 1214. For example, balls 1208 as shown in FIG. 9B would be seated in depressions 1214 as shown in FIG. 9A. This seating may be considered a magnetically-assisted kinematic coupling. Magnets 1220 may be configured to be strong enough to support the entire weight of end-effector 602 regardless of the orientation of end-effector 602. The locating coupling may be any style of kinematic mount that uniquely restrains six degrees of freedom.

With respect to the reinforcing coupling, portions of clamp 1204 may be configured to be a fixed ground link and as such clamp 1204 may serve as a five bar linkage. Closing clamp handle 1206 may fasten end-effector 602 to robot arm 604 as lip 1212 and lip 1218 engage clamp 1204 in a manner to secure end-effector 602 and robot arm 604. When clamp handle 1206 is closed, spring 1210 may be stretched or stressed while clamp 1204 is in a locked position. The locked position may be a position that provides for linkage past center. Because of a closed position that is past center, the linkage will not open absent a force applied to clamp handle 1206 to release clamp 1204. Thus, in a locked position end-effector 602 may be robustly secured to robot arm 604.

Spring 1210 may be a curved beam in tension. Spring 1210 may be comprised of a material that exhibits high stiffness and high yield strain such as virgin PEEK (polyether-ether-ketone). The linkage between end-effector 602 and robot arm 604 may provide for a sterile barrier between end-effector 602 and robot arm 604 without impeding fastening of the two couplings.

The reinforcing coupling may be a linkage with multiple spring members. The reinforcing coupling may latch with a cam or friction based mechanism. The reinforcing coupling may also be a sufficiently powerful electromagnet that will support fastening end-effector 102 to robot arm 604. The reinforcing coupling may be a multi-piece collar completely separate from either end-effector 602 and/or robot arm 604 that slips over an interface between end-effector 602 and robot arm 604 and tightens with a screw mechanism, an over center linkage, or a cam mechanism.

Figure 10:
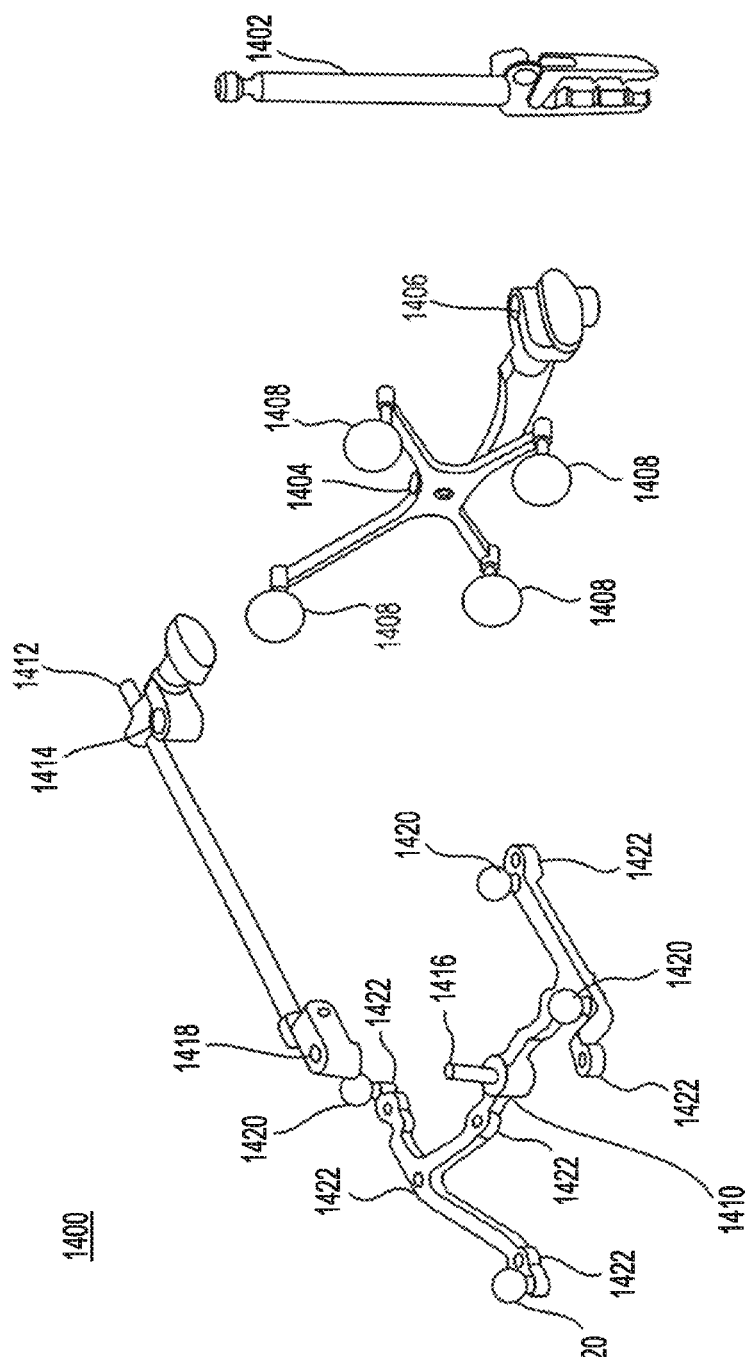
FIG. 10 illustrates a dynamic reference array, an imaging array, and other components in accordance with an exemplary embodiment.
Figure 11:
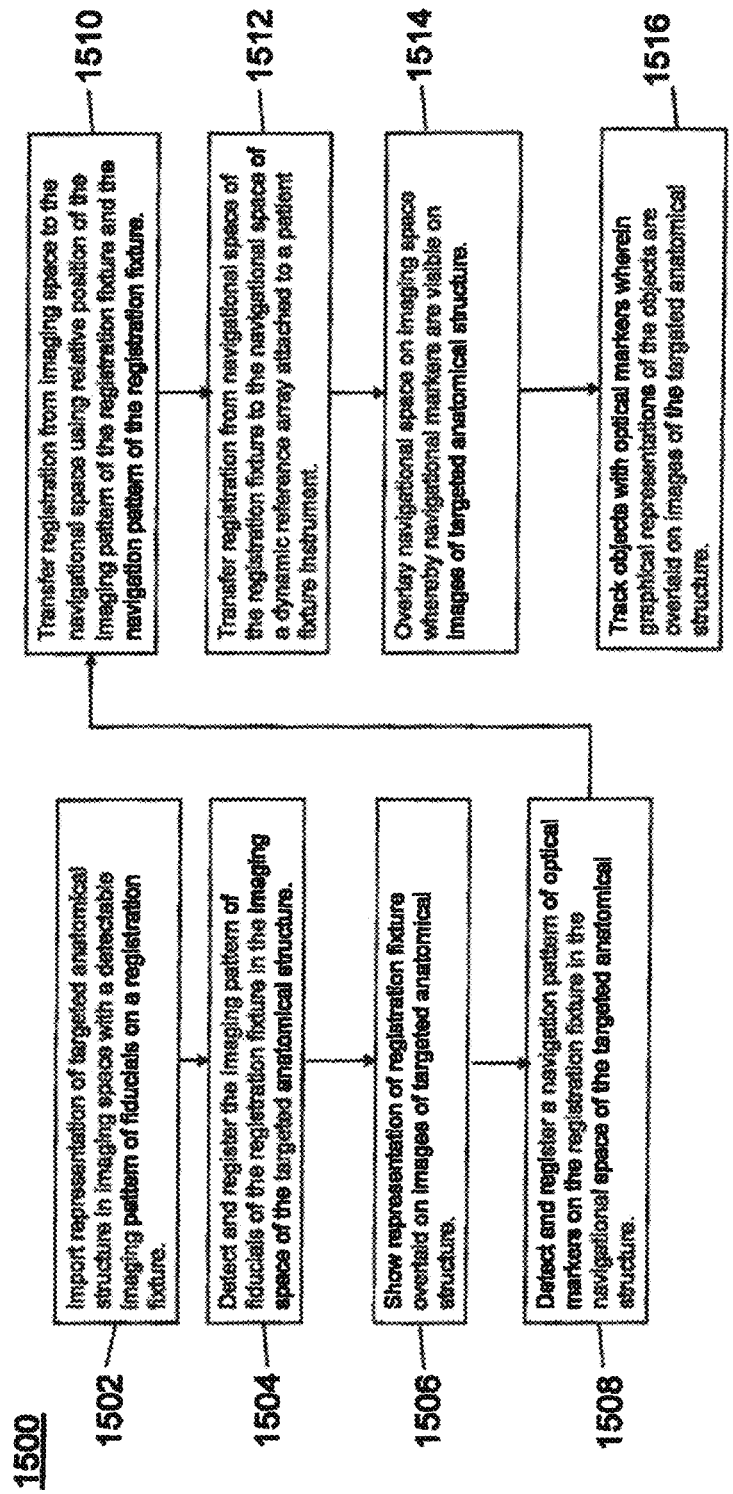
FIG. 11 illustrates a method of registration in accordance with an exemplary embodiment.

Referring to FIGS. 10 and 11, prior to or during a surgical procedure, certain registration procedures may be conducted in order to track objects and a target anatomical structure of the patient 210 both in a navigation space and an image space. In order to conduct such registration, a registration system 1400 may be used as illustrated in FIG. 10.

In order to track the position of the patient 210, a patient tracking device 116 may include a patient fixation instrument 1402 to be secured to a rigid anatomical structure of the patient 210 and a dynamic reference base (DRB) 1404 may be securely attached to the patient fixation instrument 1402. For example, patient fixation instrument 1402 may be inserted into opening 1406 of dynamic reference base 1404. Dynamic reference base 1404 may contain markers 1408 that are visible to tracking devices, such as tracking subsystem 532. These markers 1408 may be optical markers or reflective spheres, such as tracking markers 118, as previously discussed herein.

Patient fixation instrument 1402 is attached to a rigid anatomy of the patient 210 and may remain attached throughout the surgical procedure. In an exemplary embodiment, patient fixation instrument 1402 is attached to a rigid area of the patient 210, for example, a bone that is located away from the targeted anatomical structure subject to the surgical procedure. In order to track the targeted anatomical structure, dynamic reference base 1404 is associated with the targeted anatomical structure through the use of a registration fixture that is temporarily placed on or near the targeted anatomical structure in order to register the dynamic reference base 1404 with the location of the targeted anatomical structure.

A registration fixture 1410 is attached to patient fixation instrument 1402 through the use of a pivot arm 1412. Pivot arm 1412 is attached to patient fixation instrument 1402 by inserting patient fixation instrument 1402 through an opening 1414 of registration fixture 1410. Pivot arm 1412 is attached to registration fixture 1410 by, for example, inserting a knob 1416 through an opening 1418 of pivot arm 1412.

Using pivot arm 1412, registration fixture 1410 may be placed over the targeted anatomical structure and its location may be determined in an image space and navigation space using tracking markers 1420 and/or fiducials 1422 on registration fixture 1410. Registration fixture 1410 may contain a collection of markers 1420 that are visible in a navigational space (for example, markers 1420 may be detectable by tracking subsystem 532). Tracking markers 1420 may be optical markers visible in infrared light as previously described herein. Registration fixture 1410 may also contain a collection of fiducials 1422, for example, such as bearing balls, that are visible in an imaging space (for example, a three dimension CT image). As described in greater detail with respect to FIG. 11, using registration fixture 1410, the targeted anatomical structure may be associated with dynamic reference base 1404 thereby allowing depictions of objects in the navigational space to be overlaid on images of the anatomical structure. Dynamic reference base 1404, located at a position away from the targeted anatomical structure, may become a reference point thereby allowing removal of registration fixture 1410 and/or pivot arm 1412 from the surgical area.

FIG. 11 provides an exemplary method 1500 for registration consistent with the present disclosure. Method 1500 begins at step 1502 wherein a graphical representation (or image(s)) of the targeted anatomical structure may be imported into system 100, 300 600, for example computer 408. The graphical representation may be three dimensional CT or a fluoroscope scan of the targeted anatomical structure of the patient 210 which includes registration fixture 1410 and a detectable imaging pattern of fiducials 1420.

At step 1504, an imaging pattern of fiducials 1420 is detected and registered in the imaging space and stored in computer 408. Optionally, at this time at step 1506, a graphical representation of the registration fixture 1410 may be overlaid on the images of the targeted anatomical structure.

At step 1508, a navigational pattern of registration fixture 1410 is detected and registered by recognizing markers 1420. Markers 1420 may be optical markers that are recognized in the navigation space through infrared light by tracking subsystem 532 via position sensor 540. Thus, the location, orientation, and other information of the targeted anatomical structure is registered in the navigation space. Therefore, registration fixture 1410 may be recognized in both the image space through the use of fiducials 1422 and the navigation space through the use of markers 1420. At step 1510, the registration of registration fixture 1410 in the image space is transferred to the navigation space. This transferal is done, for example, by using the relative position of the imaging pattern of fiducials 1422 compared to the position of the navigation pattern of markers 1420.

At step 1512, registration of the navigation space of registration fixture 1410 (having been registered with the image space) is further transferred to the navigation space of dynamic registration array 1404 attached to patient fixture instrument 1402. Thus, registration fixture 1410 may be removed and dynamic reference base 1404 may be used to track the targeted anatomical structure in both the navigation and image space because the navigation space is associated with the image space.

At steps 1514 and 1516, the navigation space may be overlaid on the image space and objects with markers visible in the navigation space (for example, surgical instruments 608 with optical markers 804). The objects may be tracked through graphical representations of the surgical instrument 608 on the images of the targeted anatomical structure.

Figure 12A:
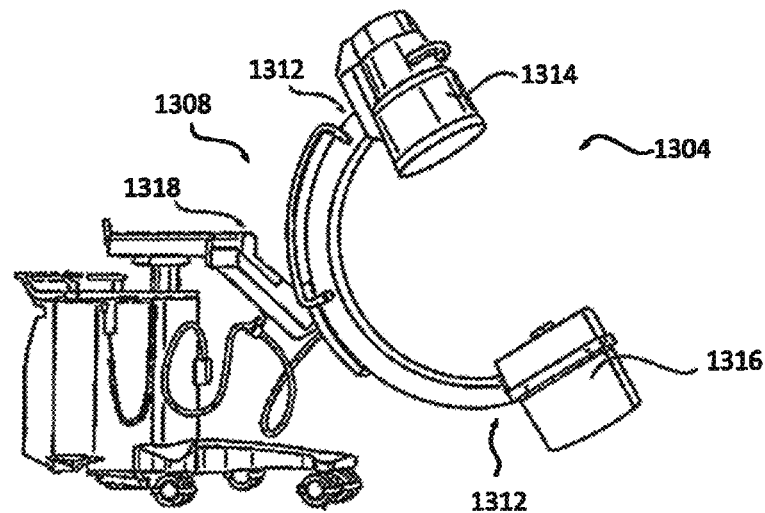
FIG. 12A-12B illustrate embodiments of imaging devices according to exemplary embodiments.
Figure 12B:
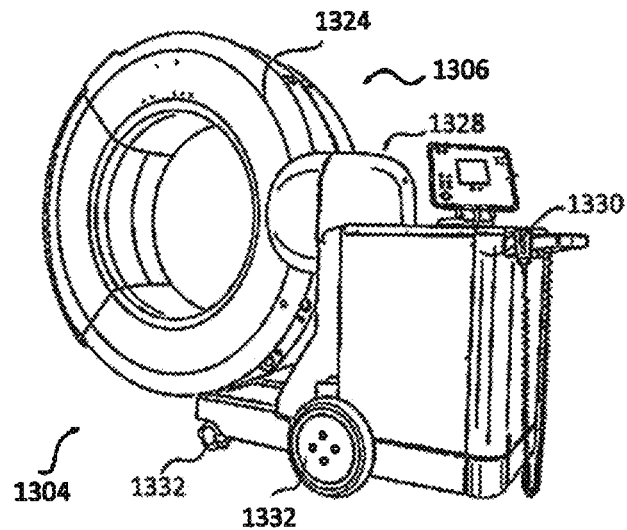

FIGS. 12A-12B illustrate imaging devices 1304 that may be used in conjunction with robot systems 100, 300, 600 to acquire pre-operative, intra-operative, post-operative, and/or real-time image data of patient 210. Any appropriate subject matter may be imaged for any appropriate procedure using the imaging system 1304. The imaging system 1304 may be any imaging device such as imaging device 1306 and/or a C-arm 1308 device. It may be desirable to take x-rays of patient 210 from a number of different positions, without the need for frequent manual repositioning of patient 210 which may be required in an x-ray system. As illustrated in FIG. 12A, the imaging system 1304 may be in the form of a C-arm 1308 that includes an elongated C-shaped member terminating in opposing distal ends 1312 of the "C" shape. C-shaped member 1130 may further comprise an x-ray source 1314 and an image receptor 1316. The space within C-arm 1308 of the arm may provide room for the physician to attend to the patient substantially free of interference from x-ray support structure 1318. As illustrated in FIG. 12B, the imaging system may include imaging device 1306 having a gantry housing 1324 attached to a support structure imaging device support structure 1328, such as a wheeled mobile cart 1330 with wheels 1332, which may enclose an image capturing portion, not illustrated. The image capturing portion may include an x-ray source and/or emission portion and an x-ray receiving and/or image receiving portion, which may be disposed about one hundred and eighty degrees from each other and mounted on a rotor (not illustrated) relative to a track of the image capturing portion. The image capturing portion may be operable to rotate three hundred and sixty degrees during image acquisition. The image capturing portion may rotate around a central point and/or axis, allowing image data of patient 210 to be acquired from multiple directions or in multiple planes. Although certain imaging systems 1304 are exemplified herein, it will be appreciated that any suitable imaging system may be selected by one of ordinary skill in the art.

Figures 13A, 13B:
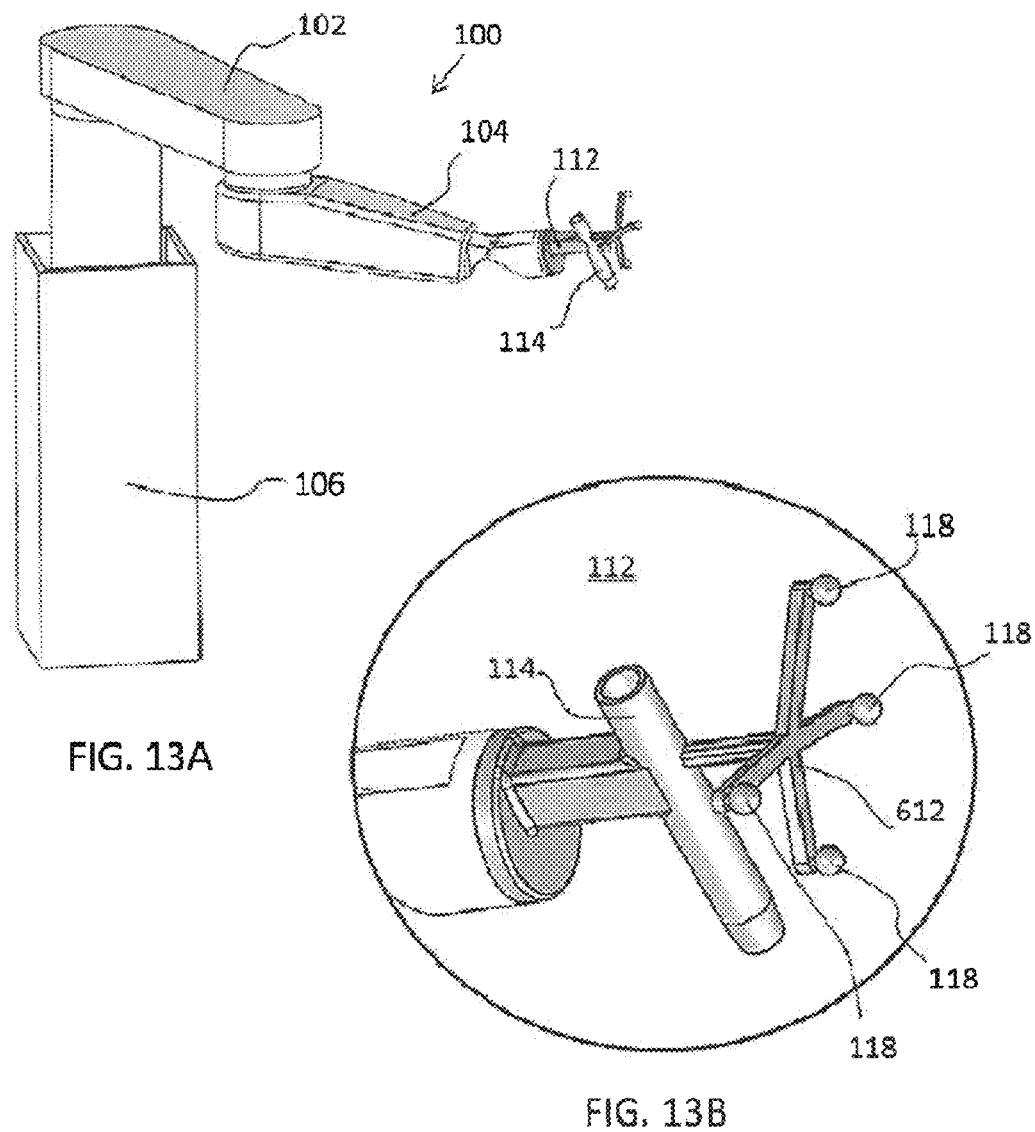
FIG. 13A illustrates a portion of a robot including the robot arm and an end-effector in accordance with an exemplary embodiment.
FIG. 13B is a close-up view of the end-effector, with a plurality of tracking markers rigidly affixed thereon, shown in FIG. 13A.
Figure 13C:
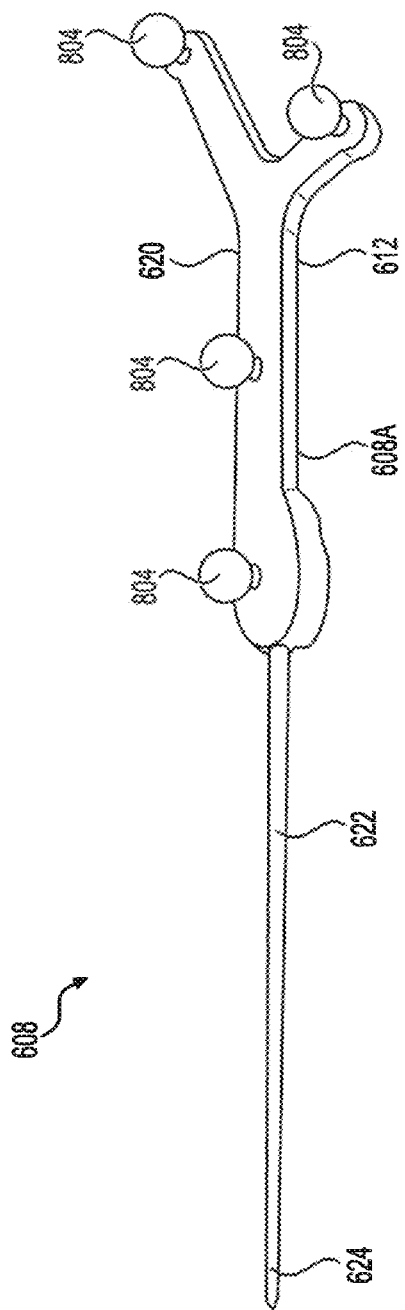
FIG. 13C is a tool or instrument with a plurality of tracking markers rigidly affixed thereon according to one embodiment.

Turning now to FIGS. 13A-13C, the surgical robot system 100, 300, 600 relies on accurate positioning of the end-effector 112, 602, surgical instruments 608, and/or the patient 210 (e.g., patient tracking device 116) relative to the desired surgical area. In the embodiments shown in FIGS. 13A-13C, the tracking markers 118, 804 are rigidly attached to a portion of the instrument 608 and/or end-effector 112.

FIG. 13A depicts part of the surgical robot system 100 with the robot 102 including base 106, robot arm 104, and end-effector 112. The other elements, not illustrated, such as the display, cameras, etc. may also be present as described herein. FIG. 13B depicts a close-up view of the end-effector 112 with guide tube 114 and a plurality of tracking markers 118 rigidly affixed to the end-effector 112. In this embodiment, the plurality of tracking markers 118 are attached to the guide tube 112. FIG. 13C depicts an instrument 608 (in this case, a probe 608A) with a plurality of tracking markers 804 rigidly affixed to the instrument 608. As described elsewhere herein, the instrument 608 could include any suitable surgical instrument, such as, but not limited to, guide wire, cannula, a retractor, a drill, a reamer, a screw driver, an insertion tool, a removal tool, or the like.

When tracking an instrument 608, end-effector 112, or other object to be tracked in 3D, an array of tracking markers 118, 804 may be rigidly attached to a portion of the tool 608 or end-effector 112. Preferably, the tracking markers 118, 804 are attached such that the markers 118, 804 are out of the way (e.g., not impeding the surgical operation, visibility, etc.). The markers 118, 804 may be affixed to the instrument 608, end-effector 112, or other object to be tracked, for example, with an array 612. Usually three or four markers 118, 804 are used with an array 612. The array 612 may include a linear section, a cross piece, and may be asymmetric such that the markers 118, 804 are at different relative positions and locations with respect to one another. For example, as shown in FIG. 13C, a probe 608A with a 4-marker tracking array 612 is shown, and FIG. 13B depicts the end-effector 112 with a different 4-marker tracking array 612.

In FIG. 13C, the tracking array 612 functions as the handle 620 of the probe 608A. Thus, the four markers 804 are attached to the handle 620 of the probe 608A, which is out of the way of the shaft 622 and tip 624. Stereophotogrammetric tracking of these four markers 804 allows the instrument 608 to be tracked as a rigid body and for the tracking system 100, 300, 600 to precisely determine the position of the tip 624 and the orientation of the shaft 622 while the probe 608A is moved around in front of tracking cameras 200, 326.

To enable automatic tracking of one or more tools 608, end-effector 112, or other object to be tracked in 3D (e.g., multiple rigid bodies), the markers 118, 804 on each tool 608, end-effector 112, or the like, are arranged asymmetrically with a known inter-marker spacing. The reason for asymmetric alignment is so that it is unambiguous which marker 118, 804 corresponds to a particular location on the rigid body and whether markers 118, 804 are being viewed from the front or back, i.e., mirrored. For example, if the markers 118, 804 were arranged in a square on the tool 608 or end-effector 112, it would be unclear to the system 100, 300, 600 which marker 118, 804 corresponded to which corner of the square. For example, for the probe 608A, it would be unclear which marker 804 was closest to the shaft 622. Thus, it would be unknown which way the shaft 622 was extending from the array 612. Accordingly, each array 612 and thus each tool 608, end-effector 112, or other object to be tracked should have a unique marker pattern to allow it to be distinguished from other tools 608 or other objects being tracked. Asymmetry and unique marker patterns allow the system 100, 300, 600 to detect individual markers 118, 804 then to check the marker spacing against a stored template to determine which tool 608, end effector 112, or other object they represent. Detected markers 118, 804 can then be sorted automatically and assigned to each tracked object in the correct order. Without this information, rigid body calculations could not then be performed to extract key geometric information, for example, such as tool tip 624 and alignment of the shaft 622, unless the user manually specified which detected marker 118, 804 corresponded to which position on each rigid body. These concepts are commonly known to those skilled in the methods of 3D optical tracking.

Figures 14A, 14B:
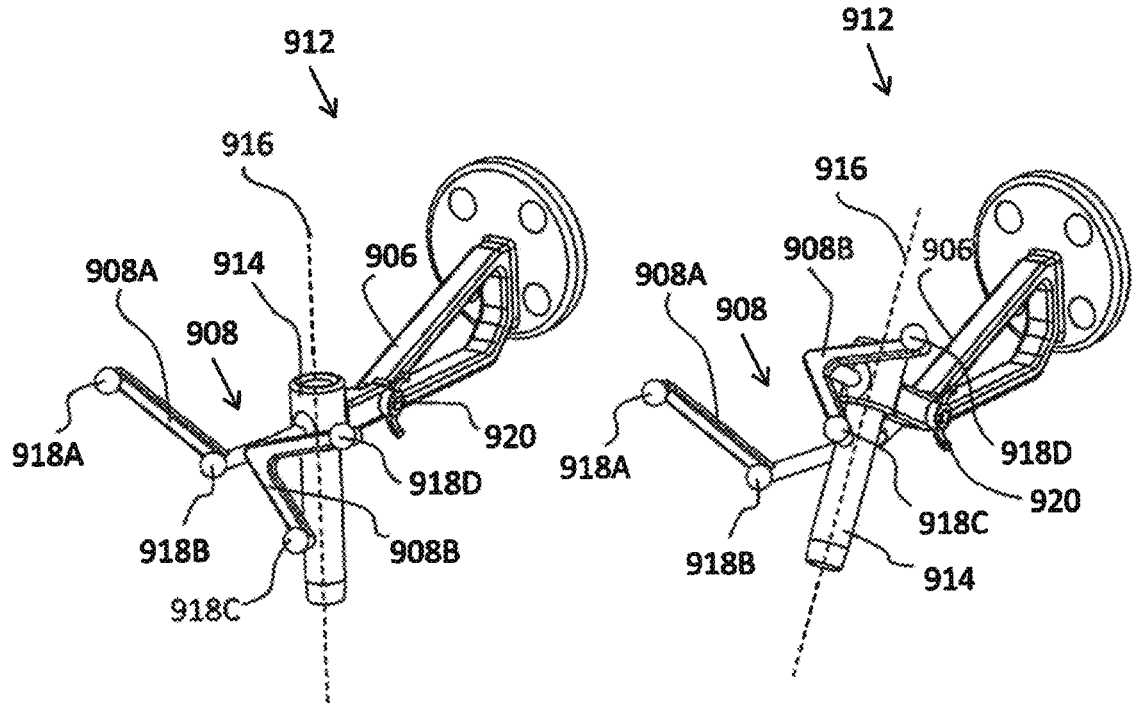
FIG. 14A is an alternative version of an end-effector with moveable tracking markers in a first configuration.
FIG. 14B is the end-effector shown in FIG. 14A with the moveable tracking markers in a second configuration.
Figure 14C:
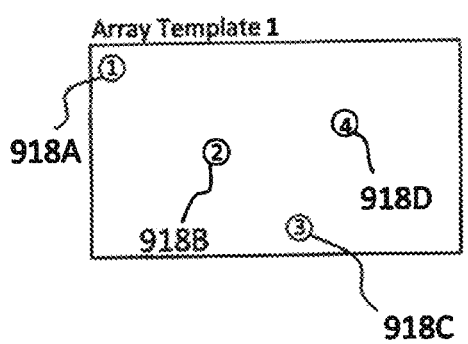
FIG. 14C shows the template of tracking markers in the first configuration from FIG. 14A.
Figure 14D:
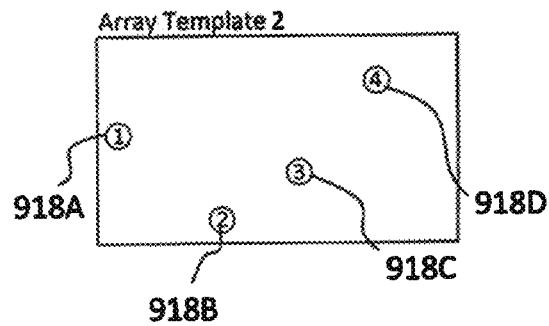
FIG. 14D shows the template of tracking markers in the second configuration from FIG. 14B.

Turning now to FIGS. 14A-14D, an alternative version of an end-effector 912 with moveable tracking markers 918A-918D is shown. In FIG. 14A, an array with moveable tracking markers 918A-918D are shown in a first configuration, and in FIG. 14B the moveable tracking markers 918A-918D are shown in a second configuration, which is angled relative to the first configuration. FIG. 14C shows the template of the tracking markers 918A-918D, for example, as seen by the cameras 200, 326 in the first configuration of FIG. 14A; and FIG. 14D shows the template of tracking markers 918A-918D, for example, as seen by the cameras 200, 326 in the second configuration of FIG. 14B.

In this embodiment, 4-marker array tracking is contemplated wherein the markers 918A-918D are not all in fixed position relative to the rigid body and instead, one or more of the array markers 918A-918D can be adjusted, for example, during testing, to give updated information about the rigid body that is being tracked without disrupting the process for automatic detection and sorting of the tracked markers 918A-918D.

When tracking any tool, such as a guide tube 914 connected to the end effector 912 of a robot system 100, 300, 600, the tracking array's primary purpose is to update the position of the end effector 912 in the camera coordinate system. When using the rigid system, for example, as shown in FIG. 13B, the array 612 of reflective markers 118 rigidly extend from the guide tube 114. Because the tracking markers 118 are rigidly connected, knowledge of the marker locations in the camera coordinate system also provides exact location of the centerline, tip, and tail of the guide tube 114 in the camera coordinate system. Typically, information about the position of the end effector 112 from such an array 612 and information about the location of a target trajectory from another tracked source are used to calculate the required moves that must be input for each axis of the robot 102 that will move the guide tube 114 into alignment with the trajectory and move the tip to a particular location along the trajectory vector.

Sometimes, the desired trajectory is in an awkward or unreachable location, but if the guide tube 114 could be swiveled, it could be reached. For example, a very steep trajectory pointing away from the base 106 of the robot 102 might be reachable if the guide tube 114 could be swiveled upward beyond the limit of the pitch (wrist up-down angle) axis, but might not be reachable if the guide tube 114 is attached parallel to the plate connecting it to the end of the wrist. To reach such a trajectory, the base 106 of the robot 102 might be moved or a different end effector 112 with a different guide tube attachment might be exchanged with the working end effector. Both of these solutions may be time consuming and cumbersome.

As best seen in FIGS. 14A and 14B, if the array 908 is configured such that one or more of the markers 918A-918D are not in a fixed position and instead, one or more of the markers 918A-918D can be adjusted, swiveled, pivoted, or moved, the robot 102 can provide updated information about the object being tracked without disrupting the detection and tracking process. For example, one of the markers 918A-918D may be fixed in position and the other markers 918A-918D may be moveable; two of the markers 918A-918D may be fixed in position and the other markers 918A-918D may be moveable; three of the markers 918A-918D may be fixed in position and the other marker 918A-918D may be moveable; or all of the markers 918A-918D may be moveable.

In the embodiment shown in FIGS. 14A and 14B, markers 918A, 918B are rigidly connected directly to a base 906 of the end-effector 912, and markers 918C, 918D are rigidly connected to the tube 914. Similar to array 612, array 908 may be provided to attach the markers 918A-918D to the end-effector 912, instrument 608, or other object to be tracked. In this case, however, the array 908 is comprised of a plurality of separate components. For example, markers 918A, 918B may be connected to the base 906 with a first array 908A, and markers 918C, 918D may be connected to the guide tube 914 with a second array 908B. Marker 918A may be affixed to a first end of the first array 908A and marker 918B may be separated a linear distance and affixed to a second end of the first array 908A. While first array 908 is substantially linear, second array 908B has a bent or V-shaped configuration, with respective root ends, connected to the guide tube 914, and diverging therefrom to distal ends in a V-shape with marker 918C at one distal end and marker 918D at the other distal end. Although specific configurations are exemplified herein, it will be appreciated that other asymmetric designs including different numbers and types of arrays 908A, 908B and different arrangements, numbers, and types of markers 918A-918D are contemplated.

The guide tube 914 may be moveable, swivelable, or pivotable relative to the base 906, for example, across a hinge 920 or other connector to the base 906. Thus, markers 918C, 918D are moveable such that when the guide tube 914 pivots, swivels, or moves, markers 918C, 918D also pivot, swivel, or move. As best seen in FIG. 14A, guide tube 914 has a longitudinal axis 916 which is aligned in a substantially normal or vertical orientation such that markers 918A-918D have a first configuration. Turning now to FIG. 14B, the guide tube 914 is pivoted, swiveled, or moved such that the longitudinal axis 916 is now angled relative to the vertical orientation such that markers 918A-918D have a second configuration, different from the first configuration.

In contrast to the embodiment described for FIGS. 14A-14D, if a swivel existed between the guide tube 914 and the arm 104 (e.g., the wrist attachment) with all four markers 918A-918D remaining attached rigidly to the guide tube 914 and this swivel was adjusted by the user, the robotic system 100, 300, 600 would not be able to automatically detect that the guide tube 914 orientation had changed. The robotic system 100, 300, 600 would track the positions of the marker array 908 and would calculate incorrect robot axis moves assuming the guide tube 914 was attached to the wrist (the robot arm 104) in the previous orientation. By keeping one or more markers 918A-918D (e.g., two markers 918C, 918D) rigidly on the tube 914 and one or more markers 918A-918D (e.g., two markers 918A, 918B) across the swivel, automatic detection of the new position becomes possible and correct robot moves are calculated based on the detection of a new tool or end-effector 112, 912 on the end of the robot arm 104.

One or more of the markers 918A-918D are configured to be moved, pivoted, swiveled, or the like according to any suitable means. For example, the markers 918A-918D may be moved by a hinge 920, such as a clamp, spring, lever, slide, toggle, or the like, or any other suitable mechanism for moving the markers 918A-918D individually or in combination, moving the arrays 908A, 908B individually or in combination, moving any portion of the end-effector 912 relative to another portion, or moving any portion of the tool 608 relative to another portion.

As shown in FIGS. 14A and 14B, the array 908 and guide tube 914 may become reconfigurable by simply loosening the clamp or hinge 920, moving part of the array 908A, 908B relative to the other part 908A, 908B, and retightening the hinge 920 such that the guide tube 914 is oriented in a different position. For example, two markers 918C, 918D may be rigidly interconnected with the tube 914 and two markers 918A, 918B may be rigidly interconnected across the hinge 920 to the base 906 of the end-effector 912 that attaches to the robot arm 104. The hinge 920 may be in the form of a clamp, such as a wing nut or the like, which can be loosened and retightened to allow the user to quickly switch between the first configuration (FIG. 14A) and the second configuration (FIG. 14B).

The cameras 200, 326 detect the markers 918A-918D, for example, in one of the templates identified in FIGS. 14C and 14D. If the array 908 is in the first configuration (FIG. 14A) and tracking cameras 200, 326 detect the markers 918A-918D, then the tracked markers match Array Template 1 as shown in FIG. 14C. If the array 908 is the second configuration (FIG. 14B) and tracking cameras 200, 326 detect the same markers 918A-918D, then the tracked markers match Array Template 2 as shown in FIG. 14D. Array Template 1 and Array Template 2 are recognized by the system 100, 300, 600 as two distinct tools, each with its own uniquely defined spatial relationship between guide tube 914, markers 918A-918D, and robot attachment. The user could therefore adjust the position of the end-effector 912 between the first and second configurations without notifying the system 100, 300, 600 of the change and the system 100, 300, 600 would appropriately adjust the movements of the robot 102 to stay on trajectory.

In this embodiment, there are two assembly positions in which the marker array matches unique templates that allow the system 100, 300, 600 to recognize the assembly as two different tools or two different end effectors. In any position of the swivel between or outside of these two positions (namely, Array Template 1 and Array Template 2 shown in FIGS. 14C and 14D, respectively), the markers 918A-918D would not match any template and the system 100, 300, 600 would not detect any array present despite individual markers 918A-918D being detected by cameras 200, 326, with the result being the same as if the markers 918A-918D were temporarily blocked from view of the cameras 200, 326. It will be appreciated that other array templates may exist for other configurations, for example, identifying different instruments 608 or other end-effectors 112, 912, etc.

In the embodiment described, two discrete assembly positions are shown in FIGS. 14A and 14B. It will be appreciated, however, that there could be multiple discrete positions on a swivel joint, linear joint, combination of swivel and linear joints, pegboard, or other assembly where unique marker templates may be created by adjusting the position of one or more markers 918A-918D of the array relative to the others, with each discrete position matching a particular template and defining a unique tool 608 or end-effector 112, 912 with different known attributes. In addition, although exemplified for end effector 912, it will be appreciated that moveable and fixed markers 918A-918D may be used with any suitable instrument 608 or other object to be tracked.

When using an external 3D tracking system 100, 300, 600 to track a full rigid body array of three or more markers attached to a robot's end effector 112 (for example, as depicted in FIGS. 13A and 13B), it is possible to directly track or to calculate the 3D position of every section of the robot 102 in the coordinate system of the cameras 200, 326. The geometric orientations of joints relative to the tracker are known by design, and the linear or angular positions of joints are known from encoders for each motor of the robot 102, fully defining the 3D positions of all of the moving parts from the end effector 112 to the base 116. Similarly, if a tracker were mounted on the base 106 of the robot 102 (not shown), it is likewise possible to track or calculate the 3D position of every section of the robot 102 from base 106 to end effector 112 based on known joint geometry and joint positions from each motor's encoder.

In some situations, it may be desirable to track the positions of all segments of the robot 102 from fewer than three markers 118 rigidly attached to the end effector 112. Specifically, if a tool 608 is introduced into the guide tube 114, it may be desirable to track full rigid body motion of the robot 902 with only one additional marker 118 being tracked.

Turning now to FIGS. 15A-15E, an alternative version of an end-effector 1012 having only a single tracking marker 1018 is shown. End-effector 1012 may be similar to the other end-effectors described herein, and may include a guide tube 1014 extending along a longitudinal axis 1016. A single tracking marker 1018, similar to the other tracking markers described herein, may be rigidly affixed to the guide tube 1014. This single marker 1018 can serve the purpose of adding missing degrees of freedom to allow full rigid body tracking and/or can serve the purpose of acting as a surveillance marker to ensure that assumptions about robot and camera positioning are valid.

The single tracking marker 1018 may be attached to the robotic end effector 1012 as a rigid extension to the end effector 1012 that protrudes in any convenient direction and does not obstruct the surgeon's view. The tracking marker 1018 may be affixed to the guide tube 1014 or any other suitable location of on the end-effector 1012. When affixed to the guide tube 1014, the tracking marker 1018 may be positioned at a location between first and second ends of the guide tube 1014. For example, in FIG. 15A, the single tracking marker 1018 is shown as a reflective sphere mounted on the end of a narrow shaft 1017 that extends forward from the guide tube 1014 and is positioned longitudinally above a mid-point of the guide tube 1014 and below the entry of the guide tube 1014. This position allows the marker 1018 to be generally visible by cameras 200, 326 but also would not obstruct vision of the surgeon 120 or collide with other tools or objects in the vicinity of surgery. In addition, the guide tube 1014 with the marker 1018 in this position is designed for the marker array on any tool 608 introduced into the guide tube 1014 to be visible at the same time as the single marker 1018 on the guide tube 1014 is visible.

Figure 15A:
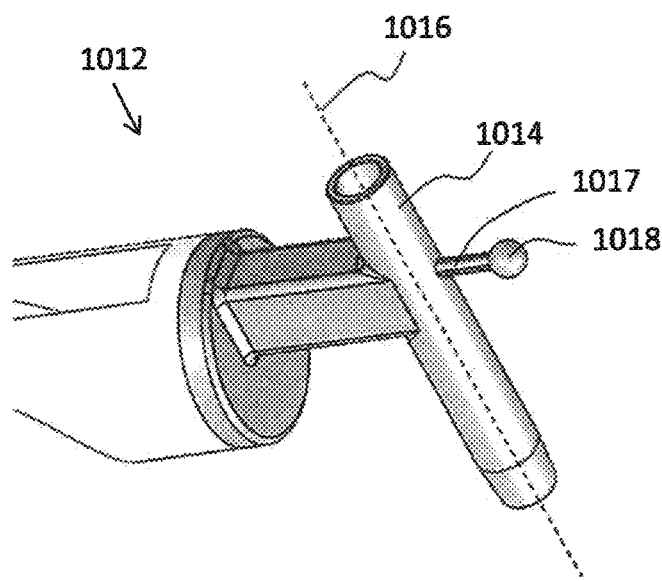
FIG. 15A shows an alternative version of the end-effector having only a single tracking marker affixed thereto.
Figure 15B:
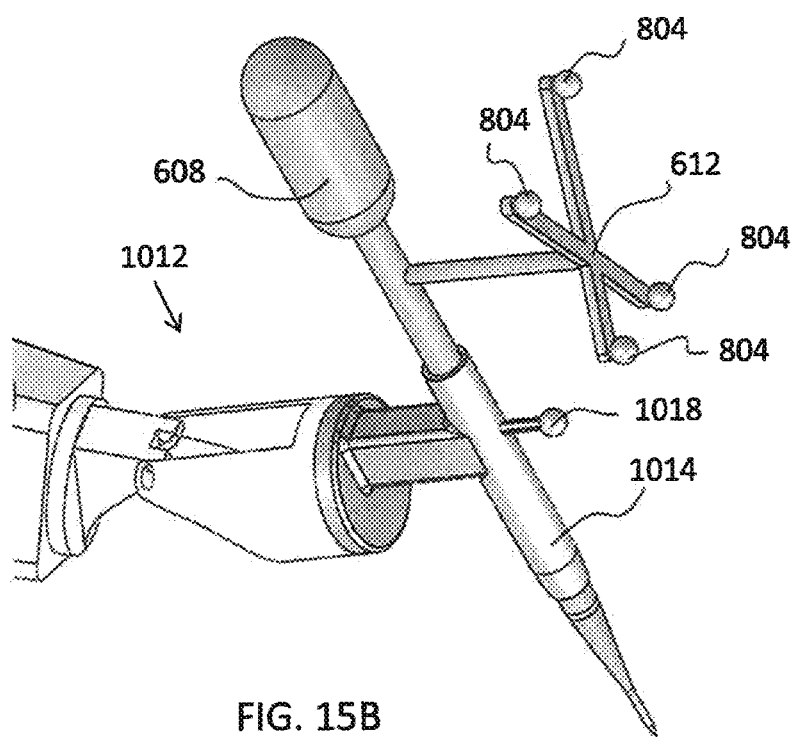
FIG. 15B shows the end-effector of FIG. 15A with an instrument disposed through the guide tube.

As shown in FIG. 15B, when a snugly fitting tool or instrument 608 is placed within the guide tube 1014, the instrument 608 becomes mechanically constrained in 4 of 6 degrees of freedom. That is, the instrument 608 cannot be rotated in any direction except about the longitudinal axis 1016 of the guide tube 1014 and the instrument 608 cannot be translated in any direction except along the longitudinal axis 1016 of the guide tube 1014. In other words, the instrument 608 can only be translated along and rotated about the centerline of the guide tube 1014. If two more parameters are known, such as (1) an angle of rotation about the longitudinal axis 1016 of the guide tube 1014; and (2) a position along the guide tube 1014, then the position of the end effector 1012 in the camera coordinate system becomes fully defined.

Figure 15C:
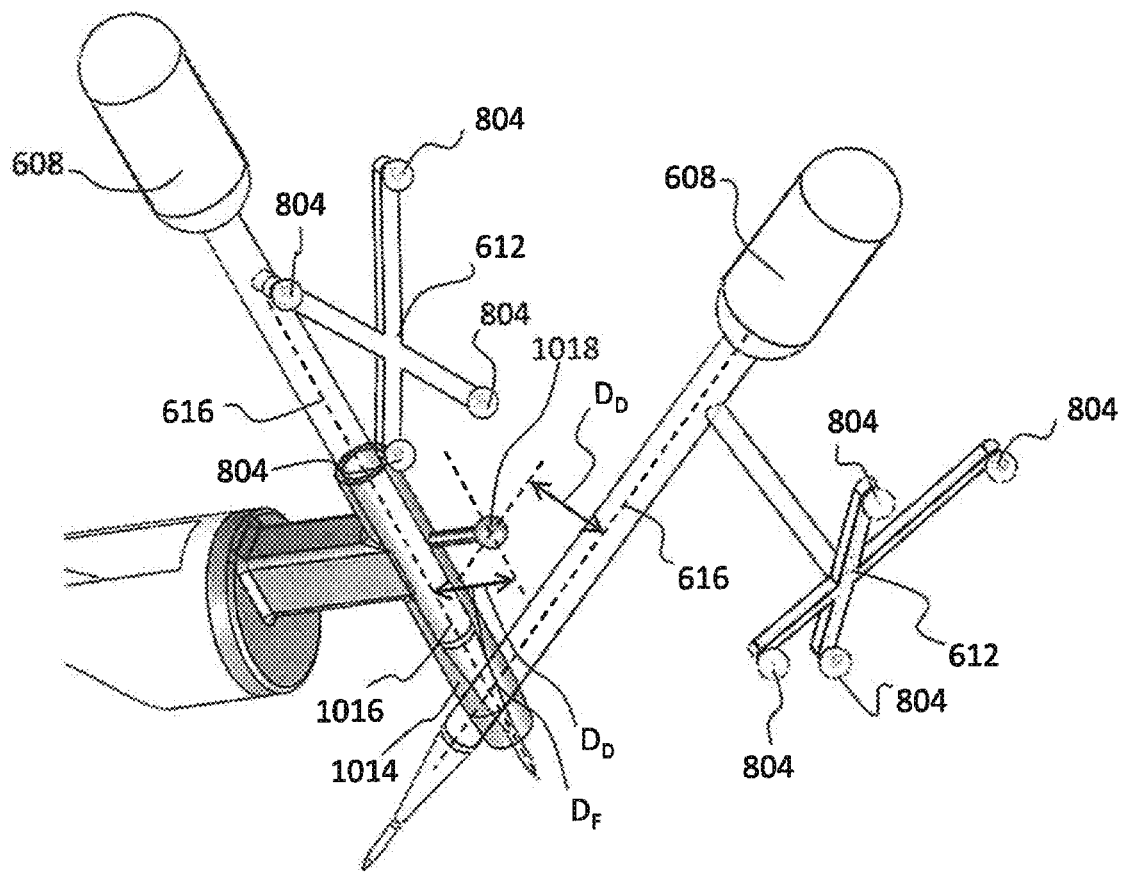
FIG. 15C shows the end-effector of FIG. 15A with the instrument in two different positions, and the resulting logic to determine if the instrument is positioned within the guide tube or outside of the guide tube.

Referring now to FIG. 15C, the system 100, 300, 600 should be able to know when a tool 608 is actually positioned inside of the guide tube 1014 and is not instead outside of the guide tube 1014 and just somewhere in view of the cameras 200, 326. The tool 608 has a longitudinal axis or centerline 616 and an array 612 with a plurality of tracked markers 804. The rigid body calculations may be used to determine where the centerline 616 of the tool 608 is located in the camera coordinate system based on the tracked position of the array 612 on the tool 608.

The fixed normal (perpendicular) distance $D_F$ from the single marker 1018 to the centerline or longitudinal axis 1016 of the guide tube 1014 is fixed and is known geometrically, and the position of the single marker 1018 can be tracked. Therefore, when a detected distance $D_D$ from tool centerline 616 to single marker 1018 matches the known fixed distance $D_F$ from the guide tube centerline 1016 to the single marker 1018, it can be determined that the tool 608 is either within the guide tube 1014 (centerlines 616, 1016 of tool 608 and guide tube 1014 coincident) or happens to be at some point in the locus of possible positions where this distance $D_D$ matches the fixed distance $D_F$. For example, in FIG. 15C, the normal detected distance $D_D$ from tool centerline 616 to the single marker 1018 matches the fixed distance $D_F$ from guide tube centerline 1016 to the single marker 1018 in both frames of data (tracked marker coordinates) represented by the transparent tool 608 in two positions, and thus, additional considerations may be needed to determine when the tool 608 is located in the guide tube 1014.

Figure 15D:
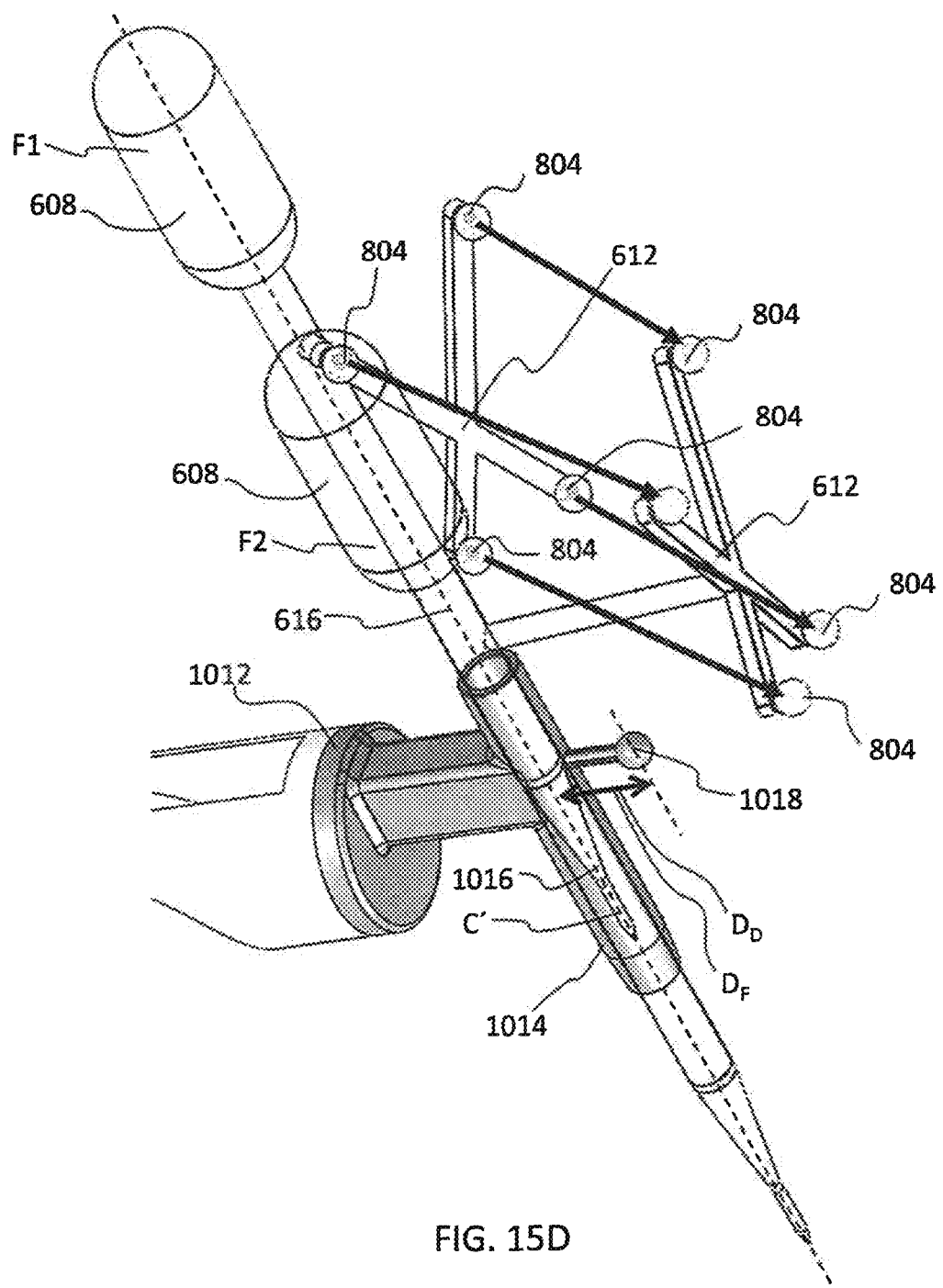
FIG. 15D shows the end-effector of FIG. 15A with the instrument in the guide tube at two different frames and its relative distance to the single tracking marker on the guide tube.

Turning now to FIG. 15D, programmed logic can be used to look for frames of tracking data in which the detected distance $D_D$ from tool centerline 616 to single marker 1018 remains fixed at the correct length despite the tool 608 moving in space by more than some minimum distance relative to the single sphere 1018 to satisfy the condition that the tool 608 is moving within the guide tube 1014. For example, a first frame F1 may be detected with the tool 608 in a first position and a second frame F2 may be detected with the tool 608 in a second position (namely, moved linearly with respect to the first position). The markers 804 on the tool array 612 may move by more than a given amount (e.g., more than 5 mm total) from the first frame F1 to the second frame F2. Even with this movement, the detected distance $D_D$ from the tool centerline vector C' to the single marker 1018 is substantially identical in both the first frame F1 and the second frame F2.

Logistically, the surgeon 120 or user could place the tool 608 within the guide tube 1014 and slightly rotate it or slide it down into the guide tube 1014 and the system 100, 300, 600 would be able to detect that the tool 608 is within the guide tube 1014 from tracking of the five markers (four markers 804 on tool 608 plus single marker 1018 on guide tube 1014). Knowing that the tool 608 is within the guide tube 1014, all 6 degrees of freedom may be calculated that define the position and orientation of the robotic end effector 1012 in space. Without the single marker 1018, even if it is known with certainty that the tool 608 is within the guide tube 1014, it is unknown where the guide tube 1014 is located along the tool's centerline vector C' and how the guide tube 1014 is rotated relative to the centerline vector C'.

Figure 15E:
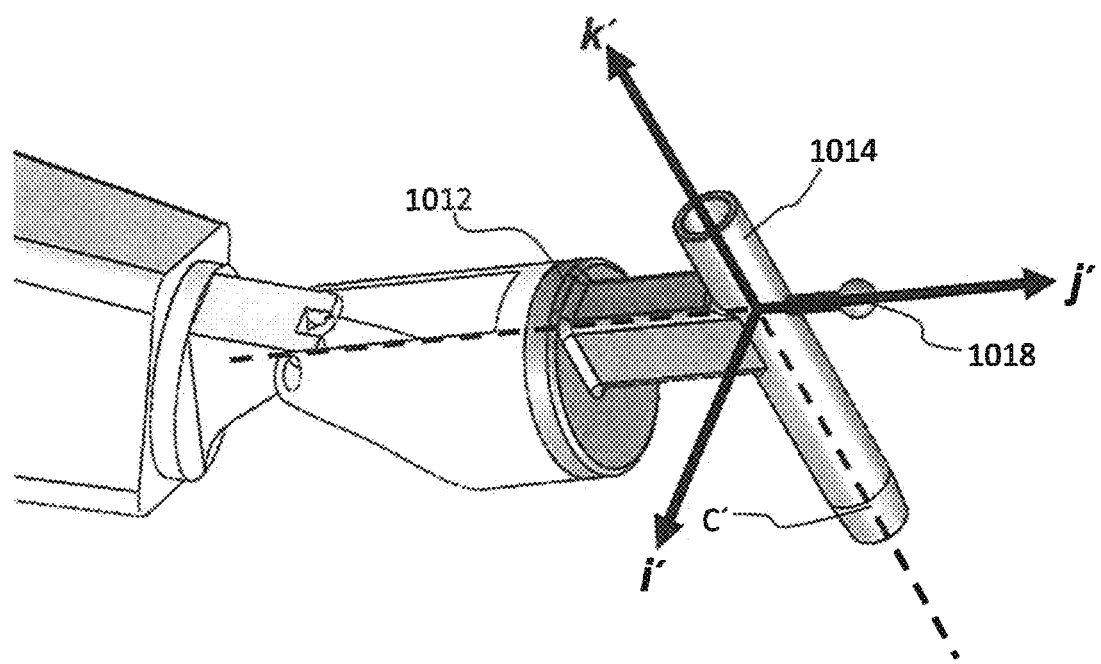
FIG. 15E shows the end-effector of FIG. 15A relative to a coordinate system.

With emphasis on FIG. 15E, the presence of the single marker 1018 being tracked as well as the four markers 804 on the tool 608, it is possible to construct the centerline vector C' of the guide tube 1014 and tool 608 and the normal vector through the single marker 1018 and through the centerline vector C'. This normal vector has an orientation that is in a known orientation relative to the forearm of the robot distal to the wrist (in this example, oriented parallel to that segment) and intersects the centerline vector C' at a specific fixed position. For convenience, three mutually orthogonal vectors k', j', i' can be constructed, as shown in FIG. 15E, defining rigid body position and orientation of the guide tube 1014. One of the three mutually orthogonal vectors k' is constructed from the centerline vector C', the second vector j' is constructed from the normal vector through the single marker 1018, and the third vector i' is the vector cross product of the first and second vectors k', j'. The robot's joint positions relative to these vectors k', j', i' are known and fixed when all joints are at zero, and therefore rigid body calculations can be used to determine the location of any section of the robot relative to these vectors k', j', i' when the robot is at a home position. During robot movement, if the positions of the tool markers 804 (while the tool 608 is in the guide tube 1014) and the position of the single marker 1018 are detected from the tracking system, and angles/linear positions of each joint are known from encoders, then position and orientation of any section of the robot can be determined.

In some embodiments, it may be useful to fix the orientation of the tool 608 relative to the guide tube 1014. For example, the end effector guide tube 1014 may be oriented in a particular position about its axis 1016 to allow machining or implant positioning. Although the orientation of anything attached to the tool 608 inserted into the guide tube 1014 is known from the tracked markers 804 on the tool 608, the rotational orientation of the guide tube 1014 itself in the camera coordinate system is unknown without the additional tracking marker 1018 (or multiple tracking markers in other embodiments) on the guide tube 1014. This marker 1018 provides essentially a "clock position" from −180° to +180° based on the orientation of the marker 1018 relative to the centerline vector C'. Thus, the single marker 1018 can provide additional degrees of freedom to allow full rigid body tracking and/or can act as a surveillance marker to ensure that assumptions about the robot and camera positioning are valid.

Figure 16:
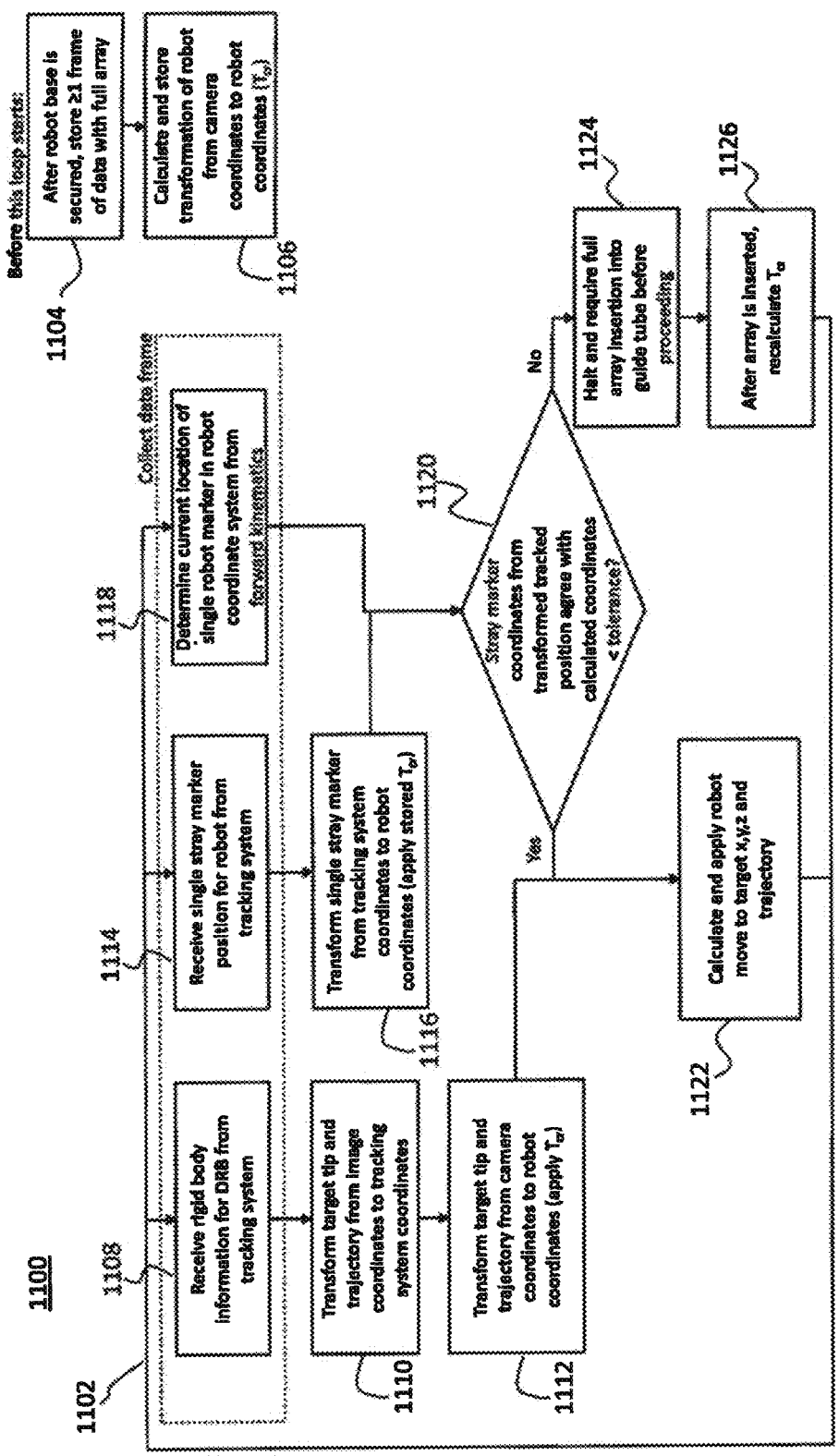
FIG. 16 is a block diagram of a method for navigating and moving the end-effector of the robot to a desired target trajectory.

FIG. 16 is a block diagram of a method 1100 for navigating and moving the end-effector 1012 (or any other end-effector described herein) of the robot 102 to a desired target trajectory. Another use of the single marker 1018 on the robotic end effector 1012 or guide tube 1014 is as part of the method 1100 enabling the automated safe movement of the robot 102 without a full tracking array attached to the robot 102. This method 1100 functions when the tracking cameras 200, 326 do not move relative to the robot 102 (i.e., they are in a fixed position), the tracking system's coordinate system and robot's coordinate system are co-registered, and the robot 102 is calibrated such that the position and orientation of the guide tube 1014 can be accurately determined in the robot's Cartesian coordinate system based only on the encoded positions of each robotic axis.

For this method 1100, the coordinate systems of the tracker and the robot must be co-registered, meaning that the coordinate transformation from the tracking system's Cartesian coordinate system to the robot's Cartesian coordinate system is needed. For convenience, this coordinate transformation can be a 4×4 matrix of translations and rotations that is well known in the field of robotics. This transformation will be termed Tcr to refer to "transformation—camera to robot". Once this transformation is known, any new frame of tracking data, which is received as x,y,z coordinates in vector form for each tracked marker, can be multiplied by the 4×4 matrix and the resulting x,y,z coordinates will be in the robot's coordinate system. To obtain Tcr, a full tracking array on the robot is tracked while it is rigidly attached to the robot at a location that is known in the robot's coordinate system, then known rigid body methods are used to calculate the transformation of coordinates. It should be evident that any tool 608 inserted into the guide tube 1014 of the robot 102 can provide the same rigid body information as a rigidly attached array when the additional marker 1018 is also read. That is, the tool 608 need only be inserted to any position within the guide tube 1014 and at any rotation within the guide tube 1014, not to a fixed position and orientation. Thus, it is possible to determine Tcr by inserting any tool 608 with a tracking array 612 into the guide tube 1014 and reading the tool's array 612 plus the single marker 1018 of the guide tube 1014 while at the same time determining from the encoders on each axis the current location of the guide tube 1014 in the robot's coordinate system.

Logic for navigating and moving the robot 102 to a target trajectory is provided in the method 1100 of FIG. 16. Before entering the loop 1102, it is assumed that the transformation Tcr was previously stored. Thus, before entering loop 1102, in step 1104, after the robot base 106 is secured, greater than or equal to one frame of tracking data of a tool inserted in the guide tube while the robot is static is stored; and in step 1106, the transformation of robot guide tube position from camera coordinates to robot coordinates Tcr is calculated from this static data and previous calibration data. Tcr should remain valid as long as the cameras 200, 326 do not move relative to the robot 102. If the cameras 200, 326 move relative to the robot 102, and Tcr needs to be re-obtained, the system 100, 300, 600 can be made to prompt the user to insert a tool 608 into the guide tube 1014 and then automatically perform the necessary calculations.

In the flowchart of method 1100, each frame of data collected consists of the tracked position of the DRB 1404 on the patient 210, the tracked position of the single marker 1018 on the end effector 1014, and a snapshot of the positions of each robotic axis. From the positions of the robot's axes, the location of the single marker 1018 on the end effector 1012 is calculated. This calculated position is compared to the actual position of the marker 1018 as recorded from the tracking system. If the values agree, it can be assured that the robot 102 is in a known location. The transformation Tcr is applied to the tracked position of the DRB 1404 so that the target for the robot 102 can be provided in terms of the robot's coordinate system. The robot 102 can then be commanded to move to reach the target.

After steps 1104, 1106, loop 1102 includes step 1108 receiving rigid body information for DRB 1404 from the tracking system; step 1110 transforming target tip and trajectory from image coordinates to tracking system coordinates; and step 1112 transforming target tip and trajectory from camera coordinates to robot coordinates (apply Tcr). Loop 1102 further includes step 1114 receiving a single stray marker position for robot from tracking system; and step 1116 transforming the single stray marker from tracking system coordinates to robot coordinates (apply stored Tcr). Loop 1102 also includes step 1118 determining current location of the single robot marker 1018 in the robot coordinate system from forward kinematics. The information from steps 1116 and 1118 is used to determine step 1120 whether the stray marker coordinates from transformed tracked position agree with the calculated coordinates being less than a given tolerance. If yes, proceed to step 1122, calculate and apply robot move to target x, y, z and trajectory. If no, proceed to step 1124, halt and require full array insertion into guide tube 1014 before proceeding; step 1126 after array is inserted, recalculate Tcr; and then proceed to repeat steps 1108, 1114, and 1118.

This method 1100 has advantages over a method in which the continuous monitoring of the single marker 1018 to verify the location is omitted. Without the single marker 1018, it would still be possible to determine the position of the end effector 1012 using Tcr and to send the end-effector 1012 to a target location but it would not be possible to verify that the robot 102 was actually in the expected location. For example, if the cameras 200, 326 had been bumped and Tcr was no longer valid, the robot 102 would move to an erroneous location. For this reason, the single marker 1018 provides value with regard to safety.

For a given fixed position of the robot 102, it is theoretically possible to move the tracking cameras 200, 326 to a new location in which the single tracked marker 1018 remains unmoved since it is a single point, not an array. In such a case, the system 100, 300, 600 would not detect any error since there would be agreement in the calculated and tracked locations of the single marker 1018. However, once the robot's axes caused the guide tube 1012 to move to a new location, the calculated and tracked positions would disagree and the safety check would be effective.

The term "surveillance marker" may be used, for example, in reference to a single marker that is in a fixed location relative to the DRB 1404. In this instance, if the DRB 1404 is bumped or otherwise dislodged, the relative location of the surveillance marker changes and the surgeon 120 can be alerted that there may be a problem with navigation. Similarly, in the embodiments described herein, with a single marker 1018 on the robot's guide tube 1014, the system 100, 300, 600 can continuously check whether the cameras 200, 326 have moved relative to the robot 102. If registration of the tracking system's coordinate system to the robot's coordinate system is lost, such as by cameras 200, 326 being bumped or malfunctioning or by the robot malfunctioning, the system 100, 300, 600 can alert the user and corrections can be made. Thus, this single marker 1018 can also be thought of as a surveillance marker for the robot 102.

It should be clear that with a full array permanently mounted on the robot 102 (e.g., the plurality of tracking markers 702 on end-effector 602 shown in FIGS. 7A-7C) such functionality of a single marker 1018 as a robot surveillance marker is not needed because it is not required that the cameras 200, 326 be in a fixed position relative to the robot 102, and Tcr is updated at each frame based on the tracked position of the robot 102. Reasons to use a single marker 1018 instead of a full array are that the full array is more bulky and obtrusive, thereby blocking the surgeon's view and access to the surgical field 208 more than a single marker 1018, and line of sight to a full array is more easily blocked than line of sight to a single marker 1018.

Turning now to FIGS. 17A-17B and 18A-18B, instruments 608, such as implant holders 608B, 608C, are depicted which include both fixed and moveable tracking markers 804, 806. The implant holders 608B, 608C may have a handle 620 and an outer shaft 622 extending from the handle 620. The shaft 622 may be positioned substantially perpendicular to the handle 620, as shown, or in any other suitable orientation. An inner shaft 626 may extend through the outer shaft 622 with a knob 628 at one end. Implant 10, 12 connects to the shaft 622, at the other end, at tip 624 of the implant holder 608B, 608C using typical connection mechanisms known to those of skill in the art. The knob 628 may be rotated, for example, to expand or articulate the implant 10, 12. U.S. Pat. Nos. 8,709,086 and 8,491,659, which are incorporated by reference herein, describe expandable fusion devices and methods of installation.

When tracking the tool 608, such as implant holder 608B, 608C, the tracking array 612 may contain a combination of fixed markers 804 and one or more moveable markers 806 which make up the array 612 or is otherwise attached to the implant holder 608B, 608C. The navigation array 612 may include at least one or more (e.g., at least two) fixed position markers 804, which are positioned with a known location relative to the implant holder instrument 608B, 608C. These fixed markers 804 would not be able to move in any orientation relative to the instrument geometry and would be useful in defining where the instrument 608 is in space. In addition, at least one marker 806 is present which can be attached to the array 612 or the instrument itself which is capable of moving within a pre-determined boundary (e.g., sliding, rotating, etc.) relative to the fixed markers 804. The system 100, 300, 600 (e.g., the software) correlates the position of the moveable marker 806 to a particular position, orientation, or other attribute of the implant 10 (such as height of an expandable interbody spacer shown in FIGS. 17A-17B or angle of an articulating interbody spacer shown in FIGS. 18A-18B). Thus, the system and/or the user can determine the height or angle of the implant 10, 12 based on the location of the moveable marker 806.

Figure 17A:
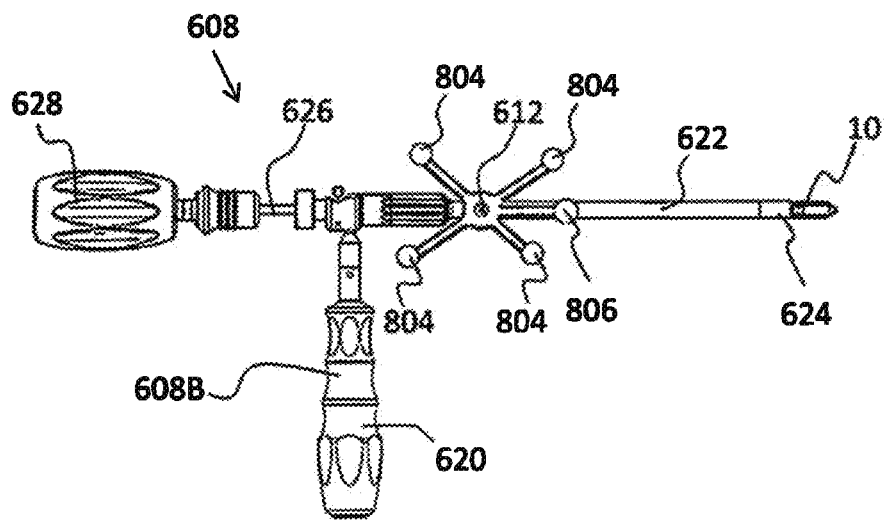
FIGS. 17A-17B depict an instrument for inserting an expandable implant having fixed and moveable tracking markers in contracted and expanded positions, respectively.
Figure 17B:
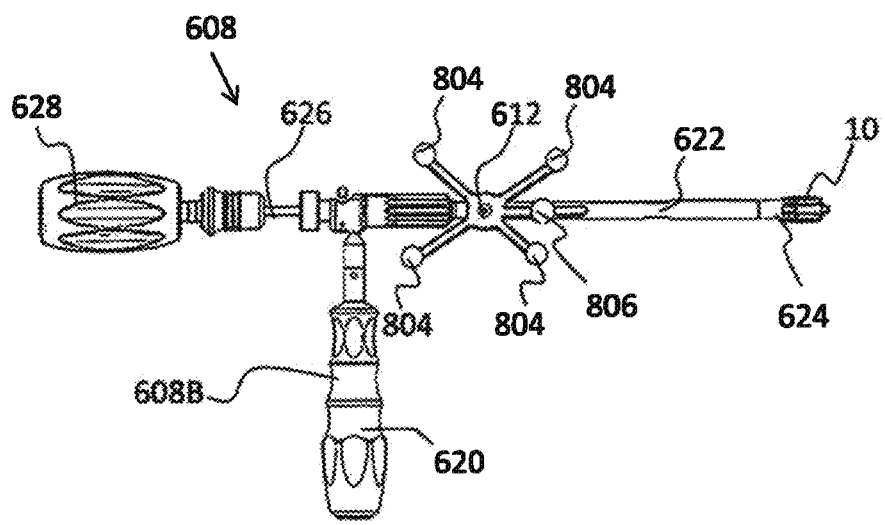

In the embodiment shown in FIGS. 17A-17B, four fixed markers 804 are used to define the implant holder 608B and a fifth moveable marker 806 is able to slide within a pre-determined path to provide feedback on the implant height (e.g., a contracted position or an expanded position). FIG. 17A shows the expandable spacer 10 at its initial height, and FIG. 17B shows the spacer 10 in the expanded state with the moveable marker 806 translated to a different position. In this case, the moveable marker 806 moves closer to the fixed markers 804 when the implant 10 is expanded, although it is contemplated that this movement may be reversed or otherwise different. The amount of linear translation of the marker 806 would correspond to the height of the implant 10. Although only two positions are shown, it would be possible to have this as a continuous function whereby any given expansion height could be correlated to a specific position of the moveable marker 806.

Figure 18A:
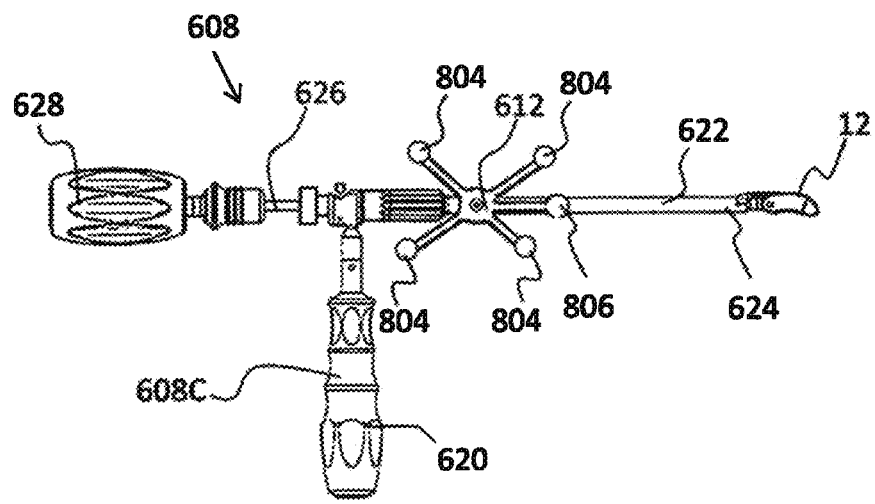
FIGS. 18A-18B depict an instrument for inserting an articulating implant having fixed and moveable tracking markers in insertion and angled positions, respectively.
Figure 18B:
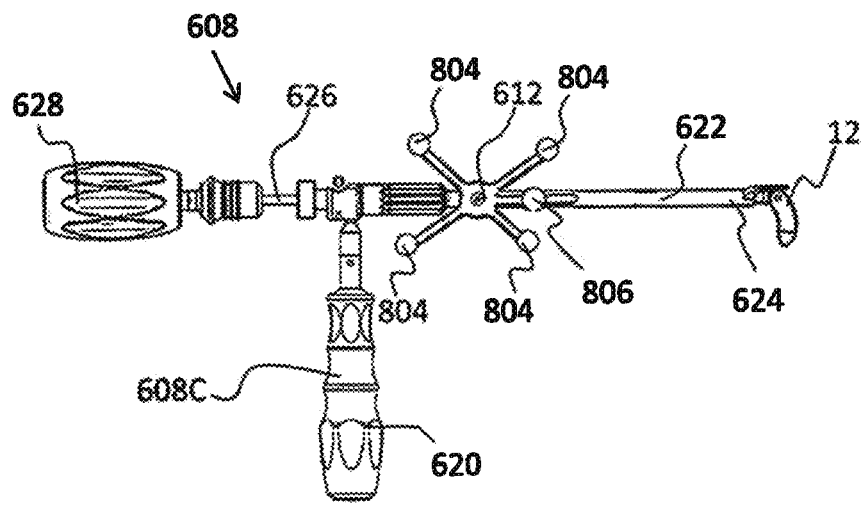

Turning now to FIGS. 18A-18B, four fixed markers 804 are used to define the implant holder 608C and a fifth, moveable marker 806 is configured to slide within a pre-determined path to provide feedback on the implant articulation angle. FIG. 18A shows the articulating spacer 12 at its initial linear state, and FIG. 18B shows the spacer 12 in an articulated state at some offset angle with the moveable marker 806 translated to a different position. The amount of linear translation of the marker 806 would correspond to the articulation angle of the implant 12. Although only two positions are shown, it would be possible to have this as a continuous function whereby any given articulation angle could be correlated to a specific position of the moveable marker 806.

In these embodiments, the moveable marker 806 slides continuously to provide feedback about an attribute of the implant 10, 12 based on position. It is also contemplated that there may be discreet positions that the moveable marker 806 must be in which would also be able to provide further information about an implant attribute. In this case, each discreet configuration of all markers 804, 806 correlates to a specific geometry of the implant holder 608B, 608C and the implant 10, 12 in a specific orientation or at a specific height. In addition, any motion of the moveable marker 806 could be used for other variable attributes of any other type of navigated implant.

Although depicted and described with respect to linear movement of the moveable marker 806, the moveable marker 806 should not be limited to just sliding as there may be applications where rotation of the marker 806 or other movements could be useful to provide information about the implant 10, 12. Any relative change in position between the set of fixed markers 804 and the moveable marker 806 could be relevant information for the implant 10, 12 or other device. In addition, although expandable and articulating implants 10, 12 are exemplified, the instrument 608 could work with other medical devices and materials, such as spacers, cages, plates, fasteners, nails, screws, rods, pins, wire structures, sutures, anchor clips, staples, stents, bone grafts, biologics, or the like.

Figure 19:
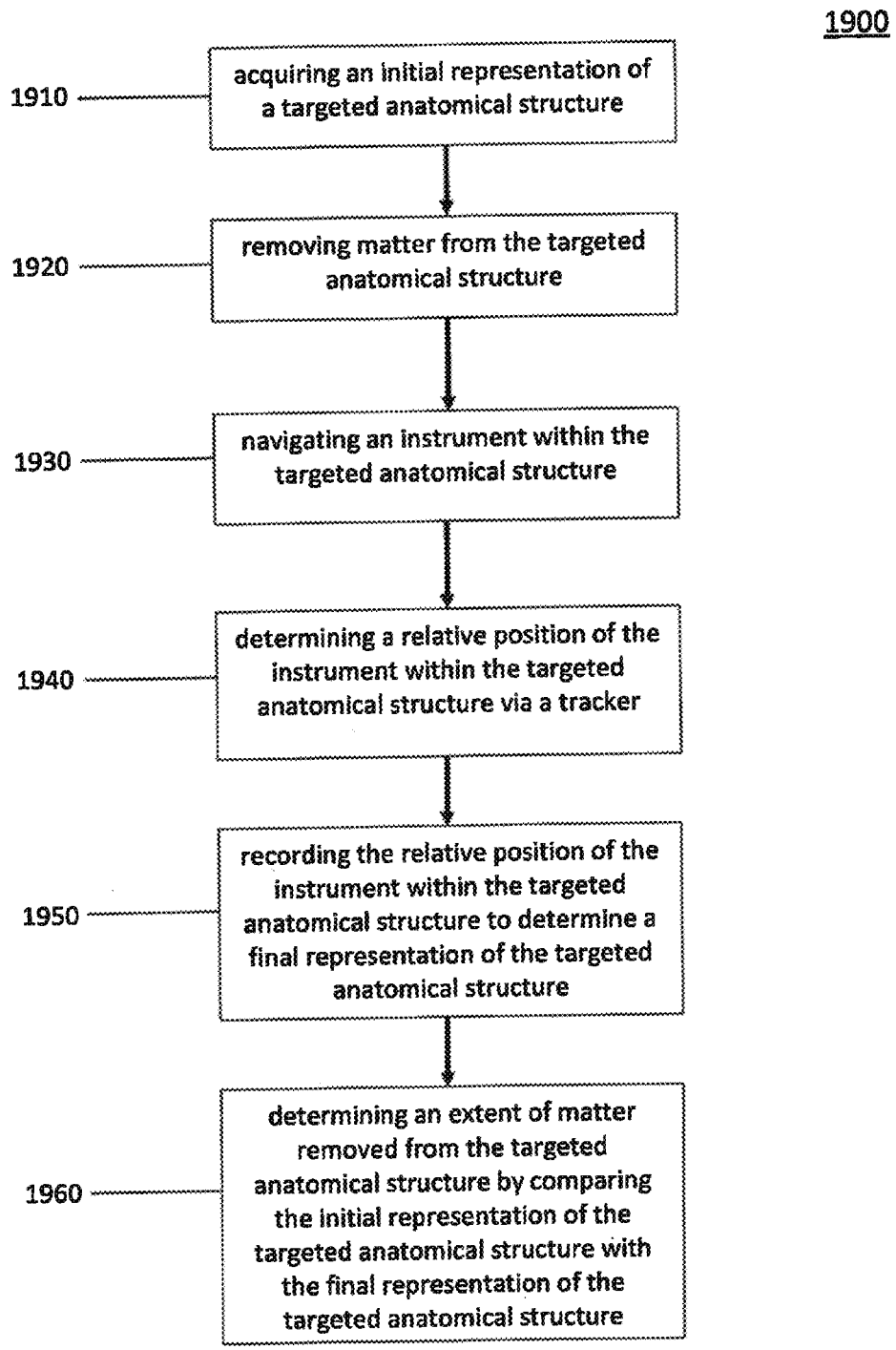
FIG. 19 illustrates a method of determining an extent of matter remaining in a targeted anatomical structure according to one embodiment.
Figure 20A:
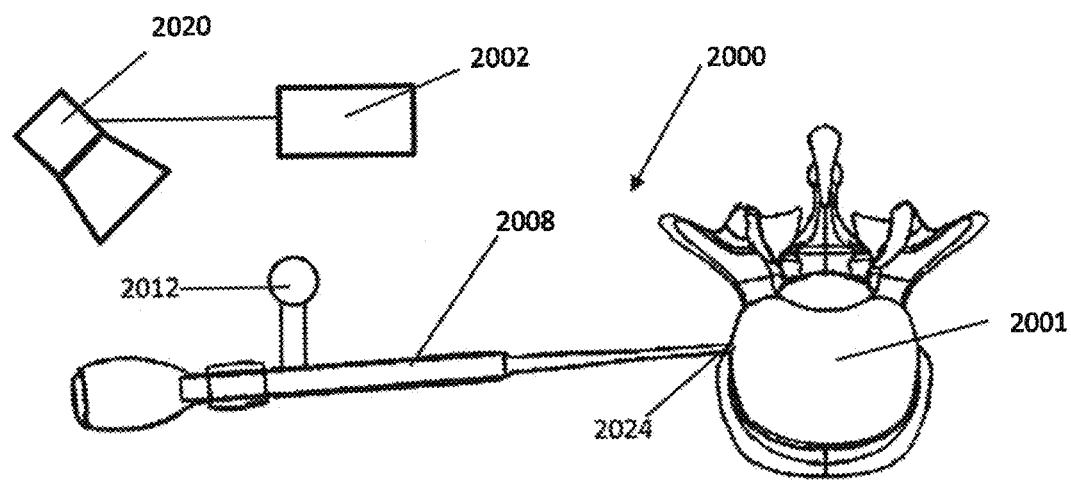
FIGS. 20A and 20B illustrate a system of determining an extent of matter remaining in a targeted anatomical structure according to an embodiment in which a tip of the instrument is tracked.
Figure 20B:
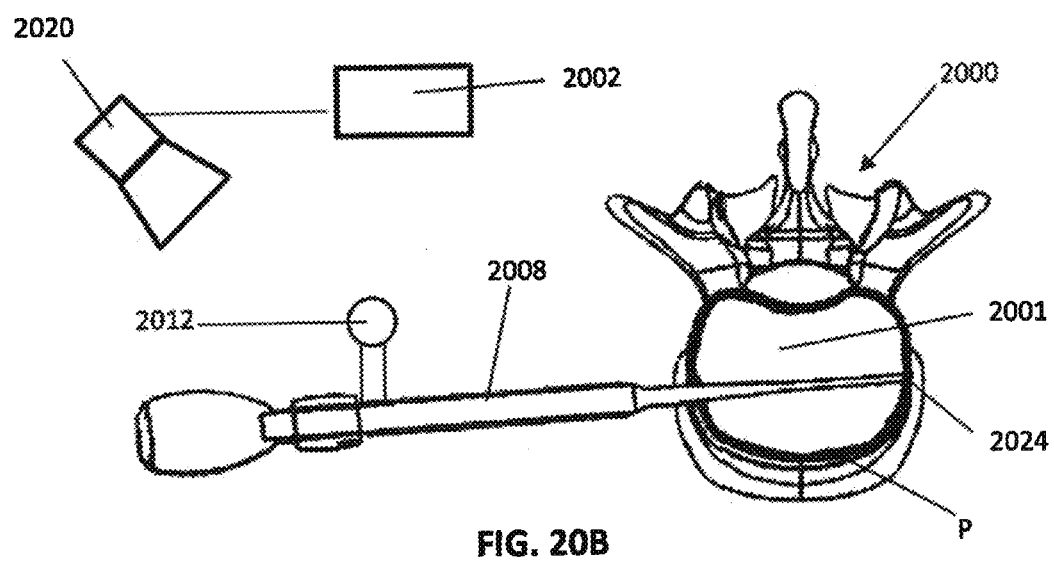

Referring to FIGS. 19, 20A, and 20B, a method 1900 and a system 2000 for determining the extent of matter, i.e. tissue and/or bone, remaining within a targeted anatomical structure 2001 of a patient is provided. In the preferred embodiment, the targeted anatomical space 2001 is preferably the disk space in a patient's spine. The method 1900 includes acquiring 1910 an initial representation of a targeted anatomical structure 2001. The acquiring step 1910 can be performed in variety of ways including, but not limited to, any one of the components or steps shown in the registration system 1400 and the procedure 1500 illustrated in FIGS. 10 and 11, the imaging devices 1304 shown in FIGS. 12A and 12B, or any other suitable imaging system as understood by one of ordinary skill in the art. The term "representation" as used herein includes any type of imaging, mapping, dataset, or other form of information.

Data for the initial representation of the targeted anatomical structure is stored by a computer system 2002, shown schematically in FIGS. 20A and 20B. The computer system 2002 can include any of the features described herein with respect to the surgical robot system 300, the computer 408, or the computer subsystem 504. The initial representation of the targeted anatomical structure 2001 includes a mapping of the patient's body. This mapping can include a three-dimensional rendering of the targeted anatomical structure, including indications, such as different colors, to represent bone matter, tissue matter, and vacant space. The initial representation of the targeted anatomical structure 2001 can be displayed by a display or screen of the computer system 2002, such as the display 110 or the display 304 described herein.

After the initial representation of the targeted anatomical structure 2001 is acquired, the method 1900 includes removing 1920 matter from the targeted anatomical structure 2001. The removal step 1920 is performed by any type of cutting, shaving, or scraping tools. The removal step 1920 is preferably performed by inserting a cutting tool in an incision near the targeted anatomical structure 2001 of the patient. In one embodiment, a surgeon performs the removal step 1920 while monitoring the position of the cutting tool via one of the tracking systems described herein. Alternatively, a robot system 100, 300, 600 can perform the removal step 1920. In another embodiment, the removal step 1920 may include the step of simultaneously monitoring and recording the position of the removal tool. As the removal of the tissue if conducted, the tissue removal is recording based on the monitored path of the instrument. Once the removal step 1920 is completed, the initial representation of the targeted anatomical structure 2001 varies from the current condition of the targeted anatomical structure 2001.

After or during the removal step 1920, the method 1900 includes navigating 1930 an instrument 2008 within the targeted anatomical structure 2001. To determine how much matter is remaining in the targeted anatomical structure 2001, The instrument 2008 is preferably a probing tool. One of ordinary skill in the art would recognize from the present disclosure that other types of surgical instruments can be used, such as a cutting tool, scraping tool, or any other type of surgical instrument. In one preferred embodiment, the navigated instrument may also be the tissue removal instrument such as the cutting tool, scraping tool or any tissue removal instrument. A surgeon can manually navigate the instrument 2008 inside the targeted anatomical structure 2001, or the instrument 2008 can be navigated with the assistance of an automated system, such as a robot system as described herein. The instrument 2008 in other embodiments may include a straight shaft for a curved shaft. In other embodiments, the instrument may include a ball tip at the distal end of the instrument. In yet other embodiments, the shaft or the distal end or both portions of the instrument may be designed to be flexible.

The instrument 2008 includes a tracking array 2012. The tracking array 2012 can include any of the features described herein with respect to the tracking array 612, or any other suitable tracking component understood by those of ordinary skill in the art. The method 1900 includes determining 1940 a relative position of the instrument 2008 within the targeted anatomical structure 2001 via the tracking array 2012. A camera 2020 tracks a position of the instrument 2008 by determining a position of the tracking array 2012. The camera 2020 can include similar features, functionality, and/or components as the cameras 200, 326 described herein.

The method 1900 includes recording 1950 the relative position of the instrument 2008 within the targeted anatomical structure 2001 to determine a final representation of the targeted anatomical structure 2001. A recorded path (P) of the instrument 2008 is shown in FIG. 20B. The recorded path (P) tracks areas within the targeted anatomical structure 2001 where the tip 2024 of the instrument 2008 has traveled. In other embodiments, any portion of the instrument may be tracked. The computer system 2002 records and processes data regarding the recorded path (P) and provides an updated image, i.e. the final representation of the targeted anatomical structure 2001.

Finally, the method 1900 includes determining 1960 the extent of matter removed from the targeted anatomical structure 2001 by comparing the initial representation of the targeted anatomical structure 2001 with the final representation of the targeted anatomical structure 2001. Multiple calculations are made regarding the delta between the initial representation and the final representation. These determinations can be performed according to a variety of processes. For example, the initial representation and the final representation of the targeted anatomical structure 2001 can be overlaid with one another by the computer system 2002 to visually illustrate how much matter has been removed. The computer system 2002 can extract data sets from the initial representation and the final representation of the targeted anatomical structure 2001 to determine dimensions, such as a thickness, of matter within the targeted anatomical structure 2001. These dimensions can be measured from the traced path of the probe, considering the diameter of the probe's tip and assuming that no volume of matter could share the space occupied by the probe tip. For example, if a probe with a spherical tip is moved in a straight line to assess whether tissue is clear, a volume represented as a cylinder of the same radius as the probe tip's radius, capped by hemispherical volumes at each end, also with the radius of the probe tip, would be the assumed space calculated to be clear of matter.

In one embodiment, the computer system 2002 is configured to provide an indicator to a user based on the relative position of the instrument 2008 within the targeted anatomical structure 2001 when the instrument 2008 approaches or encounters a boundary defined by the initial representation of the targeted anatomical structure 2001. A user can manually set borders within the targeted anatomical structure 2001 based on the initial representation. The computer system 2002 can provide a tactual, visual or auditory indicator that the instrument is approaching a boundary of the targeted anatomical structure 2001, a patient's spinal cord, or any other critical region. The indicator can include a percentage of matter remaining in the targeted anatomical structure 2001. In one embodiment, the computer system 2002 provides a dynamic indicator of the extent of matter remaining in the targeted anatomical structure 2001 during simultaneous cutting and removal of matter from the targeted anatomical structure 2001.

In another embodiment, the method 1900 includes attaching the instrument 2008 to a robotic component, such as robot arm 104. The instrument 2008 can be attached to any portion of the robotic systems 100, 300, 600. In one embodiment, the instrument 2008 is attached to an end-effector of a robot, such as end-effectors 112, 912, 1012, etc. The robotic arm can guide the instrument 2008 within the targeted anatomical structure 2001 based on data from the initial representation of the targeted anatomical structure 2001 or based on user input. The end-effector of the robot can include a guide tube, similar to guide tubes 114, 606, for receiving the instrument 2008. In one embodiment, the robotic arm can include a secondary tracking array, such as markers 702 associated with the end-effector 602, and the system 2000 can track movement of the robotic arm to further determine where the instrument 2008 has been with respect to the targeted anatomical structure 2001. The robotic arm can use data derived from comparing the initial representation of the targeted anatomical structure 2001 to the final representation of the targeted anatomical structure 2001 to navigate the instrument 2008 within the targeted anatomical structure 2001.

In one embodiment shown in FIGS. 21A-21D, a shaft 2122 of the instrument 2108 is recorded to determine where the instrument 2108 has traveled with respect to the targeted anatomical structure 2101. One of ordinary skill in the art would recognize from the present disclosure that the tip, shaft, or any other portion of the instrument can be tracked and recorded. FIG. 21 illustrates the advantage of tracking the shaft of the instrument over tracking only the tip. It can be seen from this figure that although the tip of the tool 2024 progresses around the perimeter of the disc, the central region of the disc (not numbered—shown as hatched) never encounters any portion of the instrument 2108. The system can record the path traveled by the shaft, calculate the overlap of this path with the anatomical region of interest, and display the region of the disc that is clear of matter.

Figure 22A:
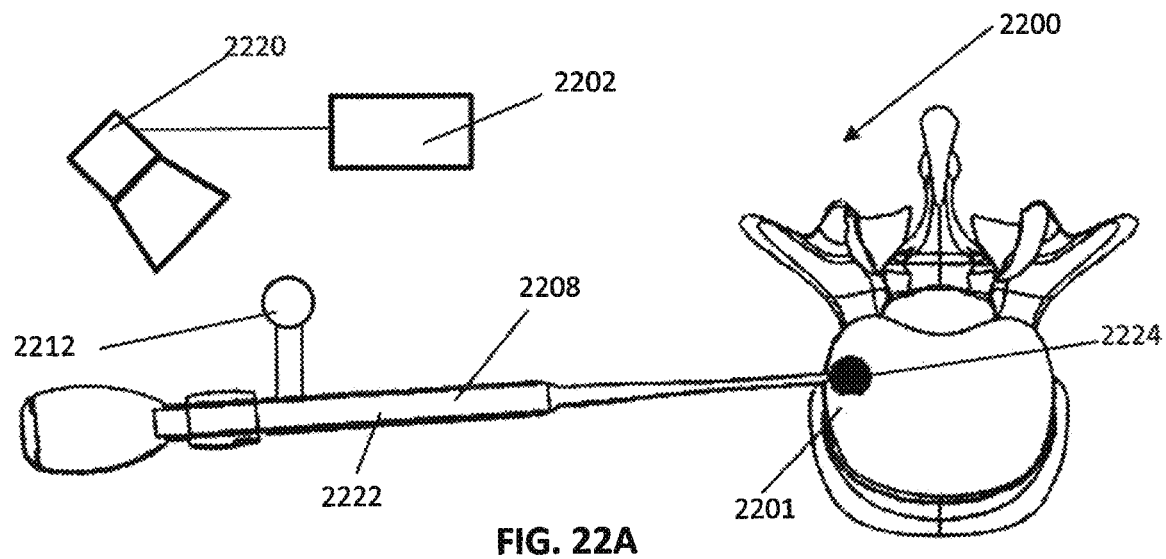
FIGS. 22A and 22B illustrate a system of determining an extent of matter remaining in a targeted anatomical structure according to an embodiment in which a tip of the instrument is enlarged.
Figure 22B:
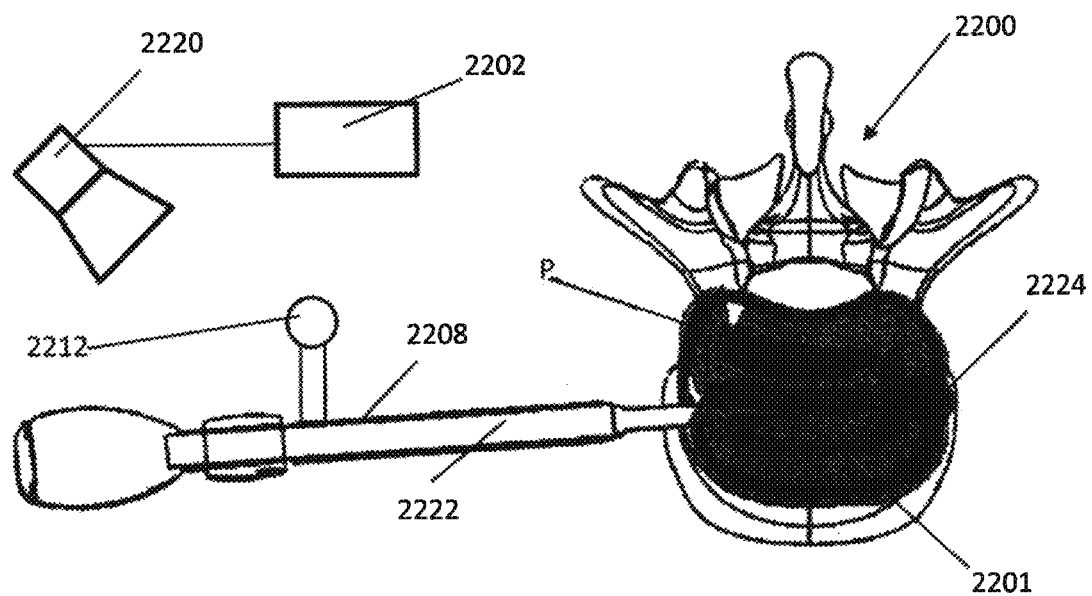

In one embodiment of the system 2200 shown in FIGS. 22A and 22B, a tip 2224 of the instrument 2208 is enlarged relative to a shaft 2222 of the instrument 2208. As shown in FIGS. 22A and 22B, the tip 2224 has a spherical profile. This enlarged tip 2224 allows a user to more quickly map the targeted anatomical structure 2201 since the tip 2224 has a relatively larger area. One of ordinary skill in the art would recognize from the present disclosure that alternative shapes of the tip 2224 can be used.

Figure 23A:
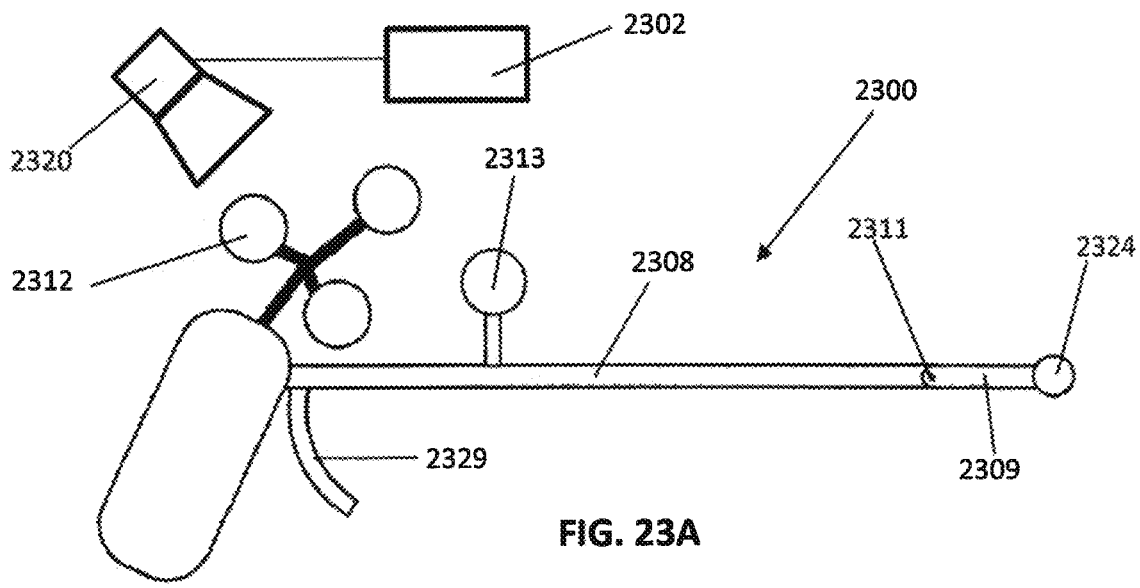
FIGS. 23A and 23B illustrate a system of determining an extent of matter remaining in a targeted anatomical structure according to an embodiment in which the instrument includes an articulable joint.
Figure 23B:
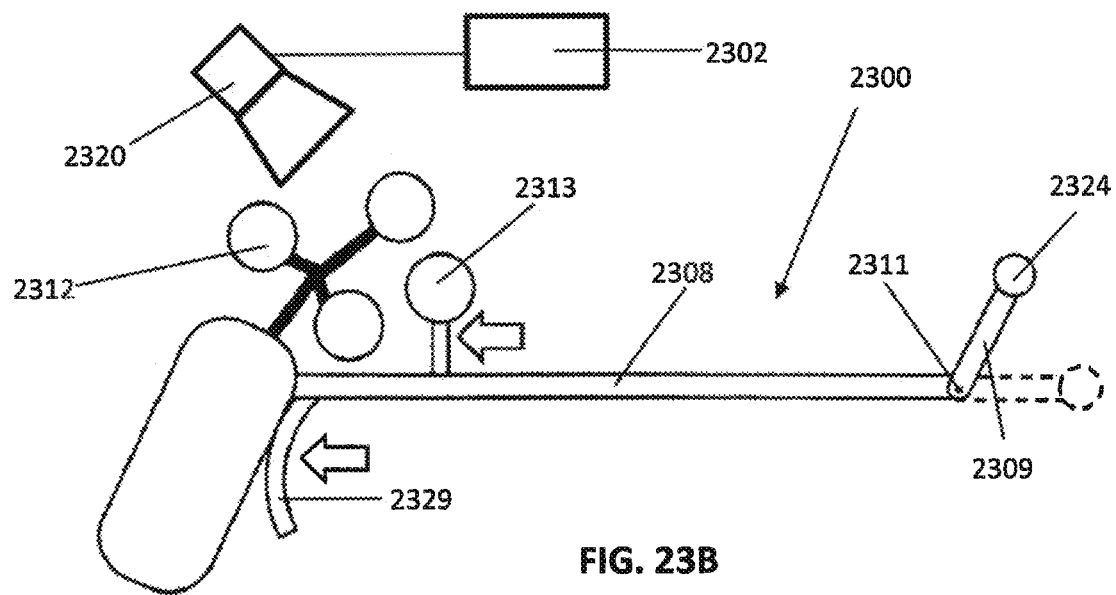

Another embodiment of the instrument 2308 is illustrated in FIGS. 23A and 23B. A terminal end 2309 of the instrument 2308 includes an articulable joint 2311. The instrument 2308 includes a secondary tracking marker 2313 configured to move relative to a primary instrument tracking array 2313 based on actuation of the articulable joint 2311. As shown in FIG. 23B, actuation of the articulable joint 2311 of the instrument 2308 pivots the tip 2324 of the instrument 2308 within the targeted anatomical structure. In one embodiment, actuation of the articulable joint 2311 is performed by squeezing a trigger 2329. One of ordinary skill in the art would recognize from the present disclosure that alternative actuators can be provided. The path traveled by the distal portion of the tool when squeezing the actuator can be traced similarly to tracing the position of the entire tool and overlaid on the anatomy to record all locations occupied by any portion of the tool. Such an articulation would be able to reach around structures and test whether matter occupies regions that are not reachable by a straight instrument. The angular position of the tip 2324 of the instrument 2308 within the targeted anatomical structure is compared to the initial representation of the targeted anatomical structure to determine the extent of matter remaining in the targeted anatomical structure. In one embodiment, the tip 2324 of the instrument 2308 can pivot from 0° to 180°. One of ordinary skill in the art would recognize from the present disclosure that the tip 2324 can have multiple degrees of freedom and could be manipulated via the trigger 2329 or additional actuators to move in multiple directions. In another embodiment, the system enables the monitoring of the position of the pivoting mechanism to determine the current position of the pivoted tip and provides this information continuously to a control unit. In another embodiment, the system is configured to assess the geometric position of the instrument and continuously tracks and records data associated with the path the instrument is moved by the user and the movement of the hinged pivot portion, thereby recording the path the instrument in moved in the x, y and z axis.

Although several embodiments of the invention have been disclosed in the foregoing specification, it is understood that many modifications and other embodiments of the invention will come to mind to which the invention pertains, having the benefit of the teaching presented in the foregoing description and associated drawings. It is thus understood that the invention is not limited to the specific embodiments disclosed hereinabove, and that many modifications and other embodiments are intended to be included within the scope of the appended claims.

It is further envisioned that features from one embodiment may be combined or used with the features from a different embodiment described herein. Moreover, although specific terms are employed herein, as well as in the claims which follow, they are used only in a generic and descriptive sense, and not for the purposes of limiting the described invention, nor the claims which follow. The entire disclosure of each patent and publication cited herein is incorporated by reference, as if each such patent or publication were individually incorporated by reference herein. Various features and advantages of the invention are set forth in the following claims.

What is claimed is:

1. A method for performing surgery using a robotic system comprising the steps of:
   providing a tracking system comprising:
      an instrument configured to be received within a targeted anatomical structure, the instrument including a tracking array, the instrument being a non-cutting tool;
      a cutting tool configured to remove at least a portion of the targeted anatomical tissue;
      at least one camera configured to detect a relative position of the instrument within the targeted anatomical structure via the tracking array; and
      a computer system and a display, the computer system configured to record the relative position of the instrument within the targeted anatomical structure as the instrument is traversed in the targeted anatomical structure after removing the at least portion of the target anatomical tissue, and to illustrate in the display a path of the traversed instrument within the targeted anatomical structure relative to an initial representation of the targeted anatomical structure based on tracking by the camera of the traversed instrument tracking array in the targeted anatomical structure;
   providing a robot arm coupled to an end effector configured to operatively connected to the instrument,
   navigating the robot arm under the guidance of the tracking system to perform a surgical procedure.

2. The method of claim 1, wherein the computer system is configured to provide an indication based on the relative position of the instrument within the targeted anatomical structure when the instrument encounters a boundary defined by the initial representation of the targeted anatomical structure.

3. The method of claim 1, wherein the computer system is configured to provide a dynamic indicator of an extent of matter remaining in the targeted anatomical structure while the cutting tool removes matter from the targeted anatomical structure.

4. The method of claim 1, wherein the end-effector includes a guide tube configured to receive the instrument.

5. The method of claim 1, wherein the robotic arm includes a secondary tracking array, and the at least one camera detects a relative position of the robotic arm to the targeted anatomical structure via the secondary tracking array.

6. The method of claim 1, wherein the robotic arm navigates the instrument within the targeted anatomical structure by comparing data regarding the path of the instrument within the targeted anatomical structure and data regarding the initial representation of the targeted anatomical structure.

7. The method of claim 1, wherein a terminal end of the instrument includes an articulable joint, and the instrument includes a secondary tracking marker configured to move relative to the tracking array based on an angle of the articulable joint.

8. The method of claim 7, wherein the articulable joint of the instrument is configured to be selectively actuated to pivot a tip of the instrument within the targeted anatomical structure, and the at least one camera detects a relative position of the tip of the instrument within the targeted anatomical structure via the secondary tracking marker.

9. The method of claim 8, wherein the computer system is configured to compare the position of the tip of the instrument relative to the targeted anatomical structure to the initial representation of the targeted anatomical structure to determine an extent of matter remaining in the targeted anatomical structure.

10. The method of claim 8, wherein the tip of the instrument is adapted to pivot from 0° to 180°.

11. The method of claim 8, wherein the instrument includes a trigger and the articulable joint is actuated by the trigger.

12. A method for determining an extent of matter removed from a targeted anatomical structure using a robotic system, comprising the steps of:
providing the robotic system with:
an instrument configured to be received within a targeted anatomical structure, the instrument including a tracking array;
detecting a relative position of the instrument within the targeted anatomical structure via the tracking array and at least one camera; and
recording the relative position of the instrument within the targeted anatomical structure, and illustrate in the display a path of the instrument within the targeted anatomical structure relative to an initial representation of the targeted anatomical structure using a computer system and a display,
wherein the targeted anatomical structure is an intervertebral disc disposed in an intervertebral space between adjacent vertebral bodies;
removing matter from the targeted anatomical structure using a cutting tool;
wherein the instrument other than the cutting tool is configured to be navigated after removing the matter with the cutting tool, within the targeted anatomical structure,
wherein the instrument is a non-cutting probing tool; and
wherein a position of a tip and shaft of the instrument within the targeted anatomical structure is determined via the tracking array by the computer system.

13. The method of claim 12, wherein the tip of the instrument is enlarged relative to a shaft of the instrument.

14. The method of claim 12, wherein the computer system is configured to determine a position of the shaft of the instrument via the tracking array for tracking the relative position of the instrument within the targeted anatomical structure.

15. The method of claim 12, wherein the computer system is configured to determine a position of the tip of the instrument for tracking the relative position of the instrument within the targeted anatomical structure.

16. The method of claim 12, wherein the computer system is configured to determine a position of the tip of the instrument and the shaft of the instrument for tracking the relative position of the instrument within the targeted anatomical structure.

17. The method of claim 12, wherein a terminal end of the instrument includes an articulable joint, and the instrument includes a secondary tracking marker configured to move relative to the tracking array based on actuation of the articulable joint, wherein the computer system is configured to compare a position of the tip of the instrument within the targeted anatomical structure to the initial representation of the targeted anatomical structure to determine the extent of matter remaining in the targeted anatomical structure.

18. The method of claim 12, further comprising navigating the instrument along an outer edge of the targeted anatomical structure.

19. The method of claim 12, wherein the instrument is a probing tool having a ball tip.

20. The method of claim 19, wherein the ball tip includes a spherical profile.

* * * * *